US010161838B2

(12) United States Patent
Huang et al.

(10) Patent No.: US 10,161,838 B2
(45) Date of Patent: Dec. 25, 2018

(54) SENSOR ASSEMBLY, METHOD, AND DEVICE FOR MONITORING SHEAR FORCE AND PRESSURE ON A STRUCTURE

(71) Applicant: Board of Regents, The University of Texas System, Austin, TX (US)

(72) Inventors: Haiying Huang, Arlington, TX (US); Hao Jiang, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 288 days.

(21) Appl. No.: 14/860,647

(22) Filed: Sep. 21, 2015

(65) Prior Publication Data
US 2016/0011091 A1 Jan. 14, 2016
US 2017/0315037 A9 Nov. 2, 2017

Related U.S. Application Data

(63) Continuation of application No. PCT/US2015/031240, filed on May 15, 2015, and a
(Continued)

(51) Int. Cl.
*H01Q 21/00* (2006.01)
*G01N 3/24* (2006.01)
(Continued)

(52) U.S. Cl.
CPC ............ *G01N 3/24* (2013.01); *A61B 5/1038* (2013.01); *A61B 5/7225* (2013.01); *A61B 5/7228* (2013.01); *G01L 19/086* (2013.01); *H01Q 21/065* (2013.01); *A61B 5/0024* (2013.01); *A61B 5/6807* (2013.01); *A61B 5/6892* (2013.01); *A61B 2562/0252* (2013.01); *A61B 2562/04* (2013.01); *A61B 2562/12* (2013.01); *G01L 5/0038* (2013.01); *G01N 2203/0025* (2013.01)

(58) Field of Classification Search
CPC ... A61B 5/1036; A61B 5/1038; A61B 5/6807; G01N 3/24; G01N 2013/0216; G01N 2203/0025; G01B 7/16; G01B 15/06; H01Q 1/2225; H01Q 21/065
See application file for complete search history.

(56) References Cited

U.S. PATENT DOCUMENTS 5,033,291 A 7/1991 Podoloff et al.
8,868,355 B2 10/2014 Huang et al.
(Continued)

OTHER PUBLICATIONS

Xu et al. "Battery-less wireless interrogation of microstrip patch antenna for strain sensing", Smart Materials and Structures, 21:125007:1-9 (2012).
(Continued)

*Primary Examiner* — Blake A Tankersley
(74) *Attorney, Agent, or Firm* — Parks IP Law LLC

(57) ABSTRACT

Shear force and pressure on a structure are simultaneously monitored using signals received from sensors with antennas on the structure. For example, sensors and systems for monitoring shear force and pressure have applications including ulcer prevention associated with structures including shoes, prosthetics, wheel-chairs, and beds of bed-bound patients.

17 Claims, 21 Drawing Sheets

Related U.S. Application Data continuation-in-part of application No. 14/180,183, filed on Feb. 13, 2014, now Pat. No. 9,138,170.

(60) Provisional application No. 61/993,327, filed on May 15, 2014, provisional application No. 61/674,201, filed on Feb. 13, 2013.

(51) Int. Cl.
*A61B 5/103* (2006.01)
*H01Q 21/06* (2006.01)
*A61B 5/00* (2006.01)
*G01L 19/08* (2006.01)
*G01L 5/00* (2006.01)

(56) References Cited

U.S. PATENT DOCUMENTS

| | | |
|---|---|---|
| 2009/0133505 A1 | 5/2009 | Sheverev et al. |
| 2010/0045551 A1 | 2/2010 | Schneider et al. |
| 2010/0162832 A1 | 7/2010 | Brauers |
| 2011/0040498 A1* | 2/2011 | Huang .................... G01B 7/16 702/34 |
| 2014/0068269 A1 | 3/2014 | Zhou |
| 2014/0230563 A1 | 8/2014 | Huang |
| 2014/0378783 A1* | 12/2014 | Ledet ...................... A61B 5/03 600/301 |

OTHER PUBLICATIONS

Mohammad et al. "Pressure and shear sensing based on microstrip antennas", Proc of SPIE vol. 8345:1D-1 thru 1D-8 (2012).

Mohammad et al. "Wireless Interrogation of Antenna Sensor to Detect Hidden Cracks", WAMICON, 5pp (Apr. 2012).

Tata et al. "Exploiting a patch antenna for strain measurements", Mes Sci Technol, 20 (2009) 015201.

International Search Report and Written Opinion issued in PCT/US2015/031240 filed May 15, 2015 (dated Aug. 17, 2015).

* cited by examiner

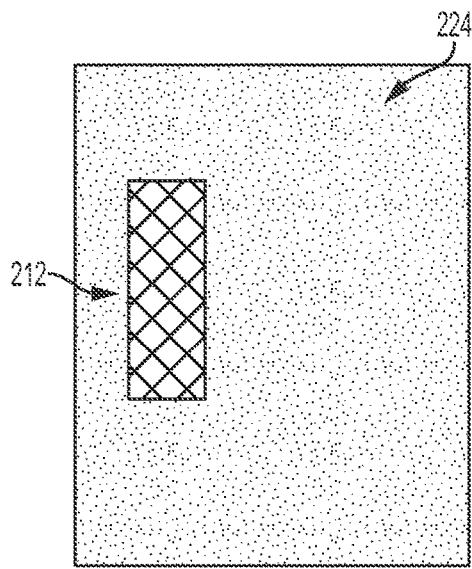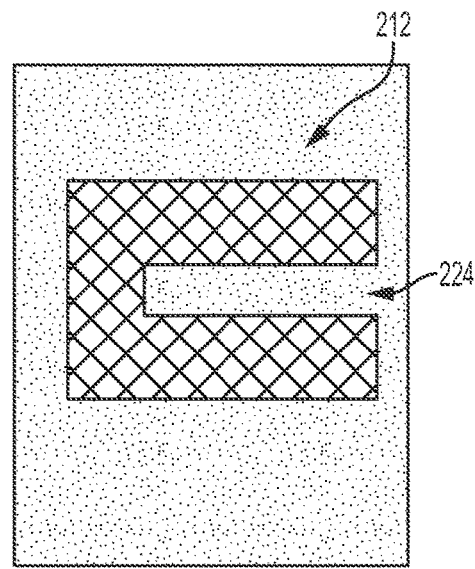
FIG. 21A  FIG. 21B
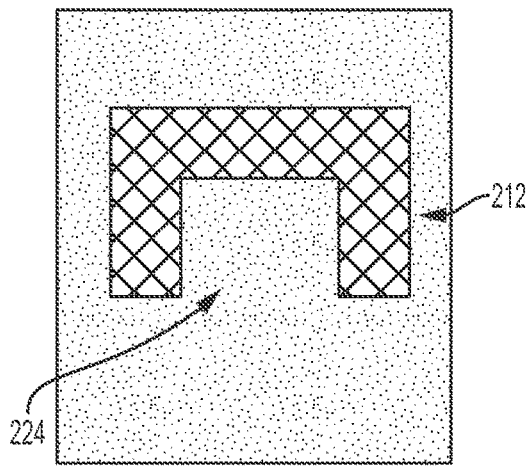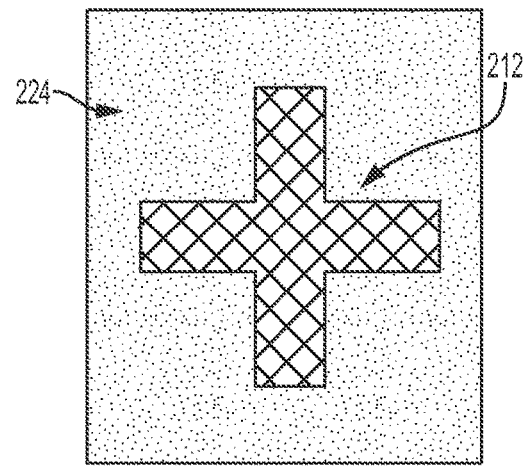
FIG. 21C  FIG. 21D

SENSOR ASSEMBLY, METHOD, AND DEVICE FOR MONITORING SHEAR FORCE AND PRESSURE ON A STRUCTURE

TECHNICAL FIELD

The present disclosure relates generally to monitoring forces on a structure and, more particularly, to monitoring shear and pressure forces on a structure using antenna sensors.

STATEMENT REGARDING GOVERNMENT-SPONSORED RESEARCH OR DEVELOPMENT

This invention was developed as part of an exploratory project funded by the Texas Medical Research Collaboration (TxMRC).

BACKGROUND

Diabetes has become a global epidemic. In the United States alone, 26.9% of the population aged 65 years or older suffers from the disease.

Foot ulcers are one of the most common complications in diabetics leading to hospitalization. 45-83% of the annual lower extremity amputations in the United States involve diabetics. The direct costs for the treatment of diabetes and its complications in the United States were more than $116 billion in 2007, among which the treatment of foot ulcers accounted for at least 33%.

Foot ulcers are the most common precursor to diabetes-related amputation. Foot ulcer prevention has become the focus of amputation prevention programs. The etiology of ulcerations in people with diabetes is commonly associated with the presence of peripheral neuropathy and unrecognized repetitive trauma.

Foot-care practitioners often use therapeutic shoes and insoles to redistribute the forces on the foot. The standard technique to evaluate their efficacy has been focused on pressure reduction, simply because in-vivo testing of shear in gait lab or clinics is not readily available. Even though peak foot pressures at the site of neuropathic ulceration have been identified as a significant risk factor for foot ulceration, elevated foot pressures are not strongly associated with predicting the development of foot ulcerations in people with diabetes and neuropathy.

The Receiver-Operating Characteristic (ROC) for neuropathic subjects with diabetes indicates that high foot pressures (>87.5 N/cm2) had a sensitivity of 63.5%, a specificity of 46.3%, a positive predictive value of 17.4% and a negative predictive value of 90.4%. This suggests that other pathologic forces on the sole of the foot, such as the shear forces, should be considered in the etiology and prevention strategy for foot ulceration.

In addition, pressure ulceration developed in superficial skins and deep tissues is a common problem encountered by diabetics, lower extremity amputees, wheelchair users, and bedridden patients. For example, 40-60% of the prosthesis users have skin problems.

A big challenge in addressing ulcers is the current lack of understanding of its etiology. It is well-established that the risks of ulceration are determined by the combination of two stress components, i.e. the pressure normal to the contact surface and the shear stress tangential to it. Even though peak foot pressures at the site of neuropathic ulceration have been identified as a significant risk factor for foot ulceration, elevated foot pressures are not strongly predictive of developing foot ulcerations in persons with diabetes and neuropathy.

Unfortunately, the role of the shear stresses is very complicated. On one hand, shear stresses are needed to prevent slippage. On the other hand, when combined with pressure, shear stresses are known to promote blood occlusion, a major cause of skin damages. Different shear stress magnitudes could also result in different types of skin damages. Small shear stresses cause rubbing that lead to skin irritation, abrasion, and/or blister formation, while large shear stresses, by preventing slippage, transfer the loads to the internal tissues.

As a result, excessive tissue deformation and stress concentrations at the tissue/bond interfaces can be generated and may eventually lead to deep tissue injuries. This is the reason why some researchers have suggested that the internal stress state instead of the superficial forces is a better indication of ulceration.

In order to calculate the internal stress state, however, both the pressure and the shear forces along the interface have to be known. Without a reliable and convenient way to measure the shear forces, scientific studies on the etiology of ulceration is severely hindered.

The availability of clinical pressure mapping system has advanced the understanding of skin ulcers and brought attention to the contribution of shear stresses. Unfortunately, the development of shear-sensing devices has been lagging behind that of pressure sensors. Despite multiple attempts in the past several decades, currently there is no shear sensor commercially available for clinical evaluations.

Several sensing mechanisms based on magneto-resistive, piezoelectric, piezoresistive, capacitive, opto-mechanical, and optical fiber sensors have been studied in the past. Some of these sensors, e.g. the magneto-resistive and piezoresistive strain sensors, have very complicated mechanical constructions and relatively large sizes. As a result, only a few sensors can be implemented in the insole to measure shear stress at critical locations. Other sensors, including the piezoelectric thin film, capacitive, and optical-based sensors, require sophisticated data conditioning and acquisition systems. Moreover, all of the conventional shear sensors require wire connections for power and data transmission. This not only limits the range of motion of the patients but also causes durability concerns if the sensors will be worn by the patients on a regular basis.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to one embodiment, a sensor assembly is provided for monitoring a shear force and pressure on a structure. The sensor assembly includes a first antenna on the structure. The first antenna is disposed on one side of a first dielectric substrate, a ground plane having a slot is disposed on an opposing side of the first dielectric substrate, and the first dielectric substrate deforms laterally in response to an applied shear force, causing a change in a resonant frequency of the first antenna.

The sensor assembly also includes a second antenna on the structure. A radiation element of second antenna is disposed on one side of a second dielectric substrate, a reflector is disposed on an opposing side of the second dielectric substrate, and the second dielectric substrate deforms vertically in response to an applied pressure force, causing a change in a resonant frequency of the second antenna.

The sensor assembly further includes a transceiver configured to receive a series of first radio frequency (RF) signals with sweeping frequencies around a first known frequency and a series of second radio frequency (RF) signal with sweeping frequencies around a second known frequency. The transceiver is also configured to transmit a first RF signal from the first antenna and a second RF signal from the second antenna. The resonant frequency or a resonant frequency shift of the first antenna is determined based on the received first RF signal, and the resonant frequency or a resonant frequency shift of the second antenna is determined based on the received second RF signal.

A lateral deformation of the first dielectric substrate is determined based on the determined resonant frequency shift of the first antenna or by comparing the determined resonant frequency of the first antenna and the first known frequency. A vertical deformation of the second dielectric substrate is determined based on the determined resonant frequency shift of the second antenna or by comparing the determined resonant frequency of the second antenna and the second known frequency. A shear force applied on the structure is determined based on the determined lateral deformation, and a pressure applied on the structure is determined based on the vertical deformation.

According to another embodiment, a method is provided for monitoring shear force and pressure on a structure. The method includes, transmitting a series of first radio frequency (RF) signals with sweeping frequencies around a first known frequency to a first antenna on the structure and transmitting a series of second radio frequency (RF) signal with sweeping frequencies around a second known frequency to a second antenna on the structure.

A radiation element of the first antenna is disposed on one side of a first dielectric substrate, a ground plane having a slot is disposed on an opposing side of the first dielectric substrate, and the first dielectric substrate deforms laterally in response to an applied shear force, causing a change in a resonant frequency of the first antenna. A radiation element of second antenna is disposed on one side of a second dielectric substrate, a reflector is disposed on an opposing side of the second dielectric substrate, and the second dielectric substrate deforms vertically in response to an applied pressure force, causing a change in a resonant frequency of the second antenna.

The method further includes receiving a first RF signal from the first antenna and a second RF signal from the second antenna, determining the resonant frequency or a resonant frequency shift of the first antenna based on the received first RF signal, determining the resonant frequency or a resonant frequency shift of the second antenna based on the received second RF signal, determining a lateral deformation of the first dielectric substrate based on the determined resonant frequency shift of the first antenna or by comparing the determined resonant frequency of the first antenna and the first known frequency, and determining a vertical deformation of the second dielectric substrate based on the determined resonant frequency shift of the second antenna or by comparing the determined resonant frequency of the second antenna and the second known frequency. The shear force applied on the structure is determined based on the determined lateral deformation, and the pressure applied on the structure is determined based on the vertical deformation.

According to another embodiment, a device is provided for monitoring shear force and pressure on a structure. The device includes a transceiver configured to transmit a series of first radio frequency (RF) signals with sweeping frequencies around a first known frequency to a first antenna on the structure and transmit a series of second radio frequency (RF) signal with sweeping frequencies around a second known frequency to a second antenna on the structure. A radiation element of the first antenna is disposed on one side of a first dielectric substrate, a ground plane having a slot is disposed on an opposing side of the first dielectric substrate, and the first dielectric substrate deforms laterally in response to an applied shear force, causing a change in a resonant frequency of the first antenna. A radiation element of second antenna is disposed on one side of a second dielectric substrate, a reflector is disposed on an opposing side of the second dielectric substrate, and the second dielectric substrate deforms vertically in response to an applied pressure force, causing a change in a resonant frequency of the second antenna. The transceiver is further configured to receive a first RF signal from the first antenna and a second RF signal from the second antenna.

The device further includes a signal processor configured to determine the resonant frequency or a resonant frequency shift of the first antenna based on the received first RF signal, determine the resonant frequency or a resonant frequency shift of the second antenna based on the received second RF signal, determine a lateral deformation of the first dielectric substrate based on the determined resonant frequency shift of the first antenna or by comparing the determined resonant frequency of the first antenna and the first known frequency, and determine a vertical deformation of the second dielectric substrate based on the determined resonant frequency shift of the second antenna or by comparing the determined resonant frequency of the second antenna and the second known frequency. The shear force applied on the structure is determined based on the determined lateral deformation. The pressure applied on the structure based on the vertical deformation.

BRIEF DESCRIPTION OF THE DRAWINGS

FIGS. 21A, 21B, 21C, and 21D illustrate plan views of schematics of antenna sensors including a reflector and a radiation patch according to illustrative embodiments.

DETAILED DESCRIPTION

Figure 1A:
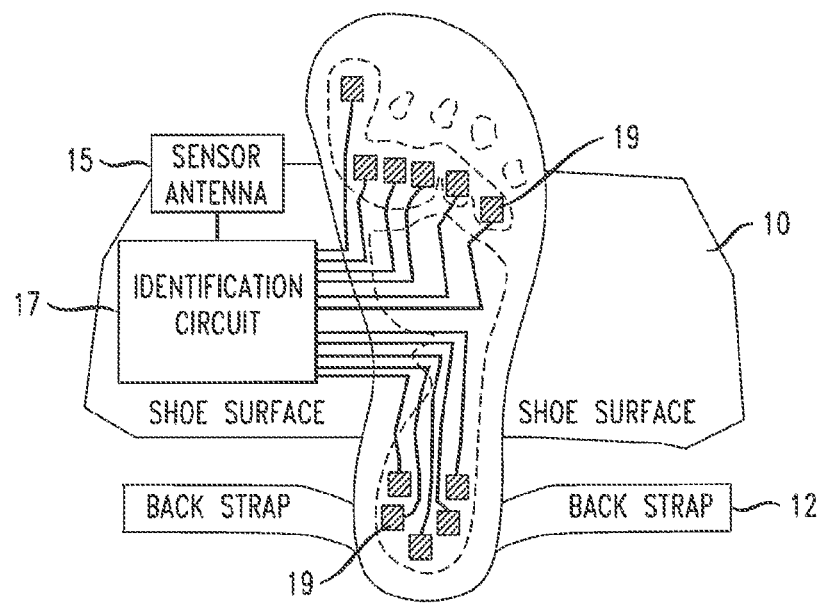
FIG. 1A illustrates a smart shoe including passive wireless antenna sensors according to an illustrative embodiment.

Detailed illustrative embodiments are disclosed herein. It must be understood that the embodiments described and illustrated are merely examples that may be embodied in various and alternative forms, and combinations thereof. As used herein, the word "illustrative" is used expansively to refer to embodiments that serve as examples or illustrations. The figures are not necessarily to scale and some features may be exaggerated or minimized to show details of particular components. Specific structural and functional details disclosed herein are not to be interpreted as limiting.

Overview

According to illustrative embodiments, a technique for in-shoe shear and pressure measurements is provided to enable quantitative studies on the pathophysiology of foot ulcers in diabetes. However, it should be appreciated that the techniques and devices described herein are not limited to in-shoe shear and pressure measurements but may be applicable to any structure for which shear and pressure measurements are useful. For example, it should be appreciated that, although part of this description is focused on in-shoe applications, shear and pressure sensors are also discussed for other applications including ulcer preventions for prosthetic wearers and wheel-chair or bed-bound patients. Particularly, the features described herein can be applied in prosthetics, for lower extremity amputees, in wheel cushions for wheelchair users, in a mattress for bedridden patients, and the like.

According to illustrative embodiments, part of the following description is directed towards design, fabrication, and characterization of in-shoe sensors and a wireless interrogation system, development and validation of a biomechanics model for internal stress calculations from measured sensor data, and an understanding of the clinical needs and the user experience of a "smart" shoe. The smart shoe may be used as a wearable assistive device that helps prevent foot ulcer in diabetic patients and provides an effective instrument for the study and understanding of skin ulceration.

The development of in-shoe shear sensors has been lagging behind that of in-shoe pressure sensors. Despite multiple attempts in the past, currently there is no in-shoe shear sensor commercially available. Sensing mechanisms based on magneto-resistive, piezoelectric, piezoresistive, capacitive, opto-mechanical, and optical fiber sensors have been studied for shear sensing in the past. Some of these sensors, e.g., the magneto-resistive and piezoresistive sensors, have very complicated mechanical constructions and relatively large sizes.

As a result, only a few sensors can be implemented in the insole to measure shear stress at critical locations. The others, including the piezoelectric thin film, capacitive, and optical-based sensors, require sophisticated data conditioning and acquisition systems. Moreover, all of the existing shear sensors require wire connections for power and data transmission, which makes them unpractical to be used by the patients on a regular basis. Current-state-of-the-art shear sensors for other applications are not readily adaptable for in-shoe applications.

This disclosure describes, among other features, a shear sensor based on passive wireless antenna sensor technology. The antenna sensor has many salient features that make it ideal for in-shoe applications. First, it can be wirelessly interrogated using a receiver located at a distance from the sensor. Second, the power consumption of the sensor circuitry is small, e.g., less than 3 $\mu$W. Third, the antenna sensor can be internally connected to sensor circuitry through microstrip transmission lines and thus do not need external wiring. Fourth, the antenna sensor may be small size with a non-obtrusive profile and can provide fine spatial resolution. Finally and perhaps most importantly, multiple antenna sensors can be interrogated with negligible latency. Combining the antenna shear sensor with a pressure sensor having similar features, detailed "mapping" of the plantar shear and pressure distribution during walking may be achieved.

From a biomechanical point of view, a skin ulcer, or the tissue "failure" in mechanics term, is governed by the local tri-axial stresses inside the tissue. In order to calculate the in-vivo stresses, however, both the pressure and the shear forces at the foot-insole interface have to be known. Without a means to measure shear forces accurately, any attempt to identify the risk factors of ulceration is severely handicapped. Providing the plantar shear and pressure distribution uniquely and completely describes the traction boundary conditions at the foot-insole interface. As a result, biomechanics based analysis models can be applied to realistically simulate the in-vivo plantar stress indices from the measurement data. This capability will lead to the formulation of a prognostic index for quantitative and objective evaluation of the patient's risk of developing foot ulcers. The technological and theoretical foundation established in this project could fundamentally change current practices of diabetic foot care and management.

Smart Shoe FIG. 1

Figure 1B:
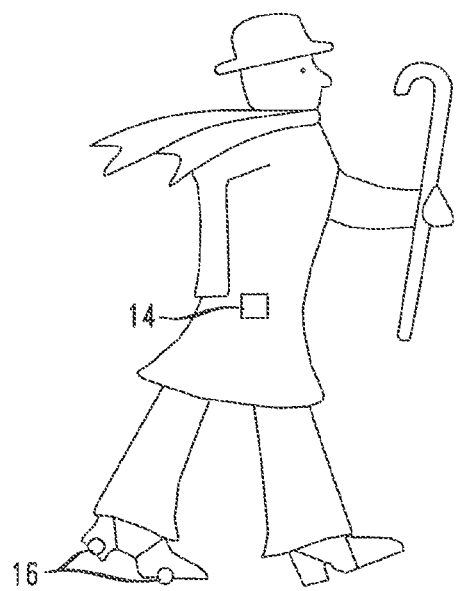
FIG. 1B illustrates implementation of a smart shoe and a wireless receiver according to an illustrative embodiment.

FIG. 1A illustrates implementation of a smart shoe, and FIG. 1B illustrates how the smart shoe may be worn and wirelessly interrogated according to an illustrative embodiment.

Referring to FIG. 1A, sensor nodes 19 may be embedded in the insole 10 of a custom-made shoe, with an expected spatial resolution of, e.g., 5×5 mm$^2$ per sensor node. The sensors nodes 19 may form a sensor array 16 and may be connected internally to an ultra-low power sensor identification circuit 17 through microstrip transmission lines. A back strap 12 may secure the sensory array embedded within the insole on the back of the foot. A sensor antenna 15, implemented on the top surface of the shoe, receives power from, and transmits the sensor information to, a receiver 14, which be secured or carried at the waist of a wearer, as shown in FIG. 1B, or on the leg of the wearer. The sensor data acquired by the receiver 14 can be either stored in a battery-powered data logger or wirelessly transmitted, as desired. A biomechanics simulation model may be used to calculate the in-vivo stresses based on the measurement data, which will provide quantified information for the study of the risk factor of ulceration and the formulation of prognostic indices.

According to an illustrative embodiment, two types of sensors may be used for sensing based on the principle of microstrip antenna technology; a patch antenna for shear sensing and a loop antenna for pressure sensing. In addition to providing compact size, low profile, high sensitivity, and fine spatial resolution, these antenna sensors can be wirelessly interrogated without needing a battery. Therefore, they are excellent candidates for in-shoe tri-axial force measurement. The design and fabrication of the patch and loop antenna sensors, as well as their characterization to detect shear and pressure, respectively, is described in detail below.

According to one embodiment, the two sensors may be vertically integrated inside a shoe to measure the shear and pressure simultaneously at the same location. This is described in more detail below with reference to FIG. 8A.

Principles of shear and pressure sensing using antenna sensors, according to illustrative embodiments, are described below. For further details of shear and pressure sensing, the reader is directed to "Pressure and shear sensing based on microstrip antennas" by I. Mohammad and H. Huang, SPIE-Smart Structures and Materials and NDE for Health Monitoring and Diagnostics, San Diego, Calif., March 2012, herein incorporated by reference.

Figure 2A:
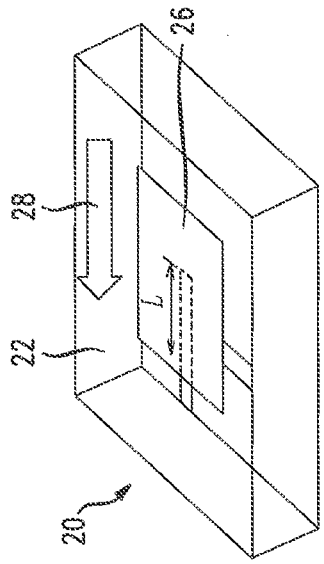
FIG. 2A illustrates a schematic of a shear detection antenna sensor according to an illustrative embodiment.
Figure 2B:
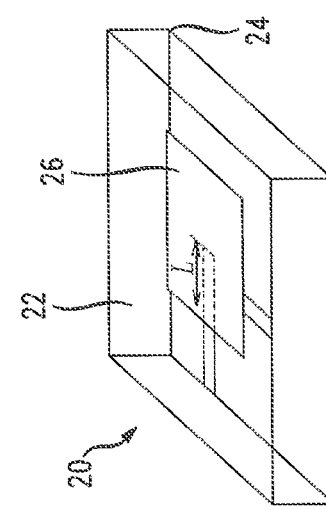
FIG. 2B illustrates a change in the position of a patch antenna due to shear force.
Figure 2C:
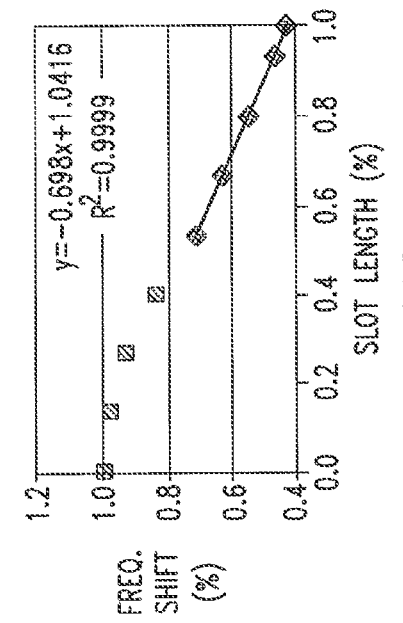
FIG. 2C illustrates an effect of a shear force on a resonant frequency of a patch antenna.
Figure 3:
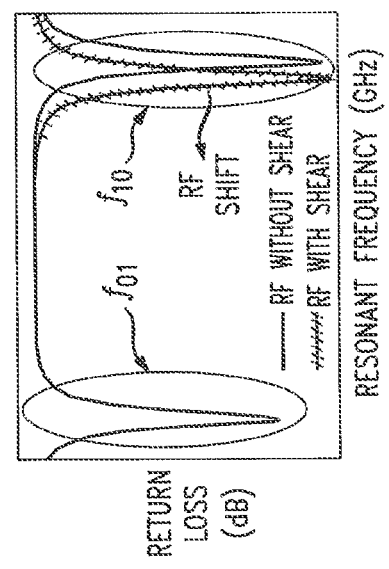
FIG. 3 illustrates graphically a relationship between a slot length in the ground plane and the frequency shift for a patch antenna according to an illustrative embodiment.

Patch Antenna Shear Sensor FIGS. 2-3

FIG. 2A illustrates a shear detection antenna sensor including a patch antenna with a slot in the ground plane according to an illustrative embodiment. As shown in FIG. 2A, the shear detection antenna sensor includes a microstrip patch antenna 20 that includes a dielectric substrate 22 with a ground plane 24 on one side and an antenna patch 26 on the other side. FIG. 2B illustrates a change in the position of the shear detection antenna sensor due to a shear force 28.

The ground plane 24 and the antenna patch 26, both conductive in nature, form an electromagnetic resonant cavity that radiates at distinct frequencies. The radiation characteristics of the antenna sensor can be represented by the $S_{11}$ curves shown in FIG. 2C, which illustrates return loss as a function of resonant frequency. If the antenna patch 26 is rectangular, it radiates at two fundamental resonant modes; the $TM_{10}$ mode, whose electric field is parallel to the physical width of the antenna patch, and the $TM_{01}$ mode, whose electric field is parallel to the physical length of the antenna patch. The resonant frequencies ($f_{10}$ and $f_{01}$) of these modes ($TM_{10}$ and $TM_{01}$) are related to the corresponding electric field dimension as:

$$f = \frac{c}{\sqrt{\varepsilon_e}} \frac{1}{L_e + 2\Delta L_c} \quad (1)$$

where f is the resonant frequency, c is the velocity of light in a vacuum, εe is the effective dielectric constant of the substrate, ΔLe is the line extension, and Le is the electric length of antenna, which is the geometrical dimension of the antenna patch that is parallel to the respective electric current direction. Therefore, a rectangular antenna patch having a larger dimension along the length direction will have a lower TM01 resonant frequency f01 and a higher TM10 resonant frequency f10. Based on equation 1, the relationship between the applied strain εL and the antenna frequency shift may be given as:

$$\varepsilon L = C \Delta f / f \quad (2)$$

where $\Delta f = f - f0$ in which f is the antenna frequency at strain εL, and f0 is the antenna frequency at zero strain, and C is a constant that is related to the dielectric constants and the physical parameters of the antenna sensor (e.g. the effective dielectric constant, the substrate thickness, the electrical width of the patch, and the velocity of light c. A positive strain εL will shift the antenna resonant frequency to a lower frequency due to the elongation of the electrical length, i.e. C is negative.

When a slot is introduced in the ground plane 24 of the antenna sensor 20, e.g., along the length direction of the antenna patch 26, it partially cuts off the current flow along the width direction and forces the current to flow around the slot. As a result, the current path along the width direction is increased, essentially increasing the electrical length of the $TM_{10}$ mode. Since the resonant frequency is inversely proportional to the electrical length, the resonant frequency $f_{10}$ reduces as the overlap length between the patch and the slot increases. The amount of reduction in the $f_{10}$ frequency is determined by the overlap length between the slot and the patch.

According to an illustrative embodiment, this characteristic of the patch antenna sensor may be utilized to measure shear deformation. As shown in FIG. 2B, a shear force 28 applied on the patch 26 causes the substrate 22 to deform laterally and shifts the position of the antenna patch. This increases the overlap length between the slot and the patch, resulting in the $f_{10}$ frequency shift of the antenna, as shown in FIG. 2C. Similarly, the shear acting perpendicular to the width of the patch antenna sensor can be evaluated by adding a slot perpendicular to the length of the patch and monitoring the $f_{01}$ frequency of the antenna sensor. In this manner, shear deformation of the substrate 22 due to foot interaction in either direction may be measured.

The selection of the initial slot length may be determined based on the relationship between the slot overlapping length and the antenna frequency shift for a slot perpendicular to the patch width, which is given as:

$$f_{10} = -0.6098\tilde{l} + 1.0416 \quad (3)$$

where $f_{10}$ is the normalized $f_{10}$ frequency with respect to the $f_{10}$ frequency when there is no slot in the ground plane, and $\tilde{l}$ is the overlapping length between the slot and the patch, normalized with respect to the patch length. As can be seen from FIG. 3, which illustrates the relationship between the frequency shift and the slot length, the resonant frequency shift is linear when the overlapping length is greater than 50% of the patch length, i.e. $\sim>0.5$.

Two of the design parameters for the shear detection antenna sensor are the maximum shear deformation and the area covered by the sensor. In experimental trials, the maximum shear deformation measured was reported to be less than 5 mm full scale (i.e., ±2.5 mm). As discussed above, a linear response is obtained when the overlapping length of the slot is more than 50%. Therefore, a patch antenna sensor with a length of more than 10 mm is desirable.

Another important criterion is the amount of area covered by a single shear sensor. A single shear sensor which covers an approximate area of 2 $cm^2$ is desired to measure shear at a point. To simplify the design, the patch dimensions were rounded up to be 15 mm in length and 12.5 mm in width (i.e., an approximate area of 1.87 $cm^2$).

The material, size and shape of the substrate were based on the maximum shear stress to be monitored and the hysteresis of the substrate. A Poron® substrate was chosen due to its low hysteresis and high flexibility. The substrate was cut into a 16 mm long and 14 mm wide rectangular pillar to support the antenna patch, which allows a larger lateral deformation of the substrate. The thickness of the Poron® substrate was selected to be 9.5 mm.

Loop Antenna Pressure Sensor FIG. 4

Figure 4A:
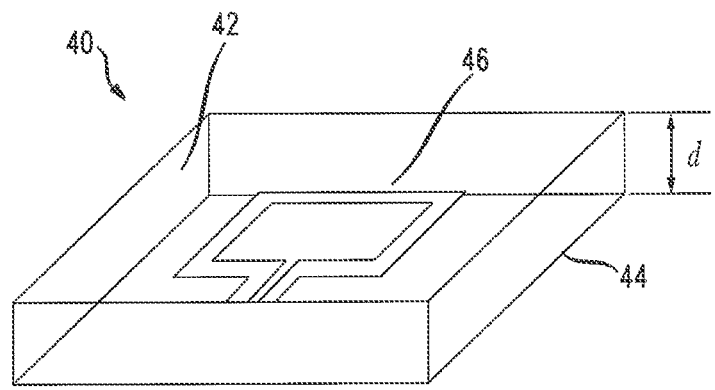
FIG. 4A illustrates a schematic view of a pressure detection antenna sensor according to an illustrative embodiment.

FIG. 4A illustrates a pressure detection antenna sensor including a loop antenna according to an illustrative embodiment. The pressure detection antenna sensor includes a dielectric substrate 42, a loop antenna 46 printed on one side of the substrate, and a reflector 44 on the other side of the dielectric substrate. The loop antenna 46 on one side of the substrate 42 is separated from the reflector 44 on the other side of the substrate 42 by a distance d.

Figure 4B:
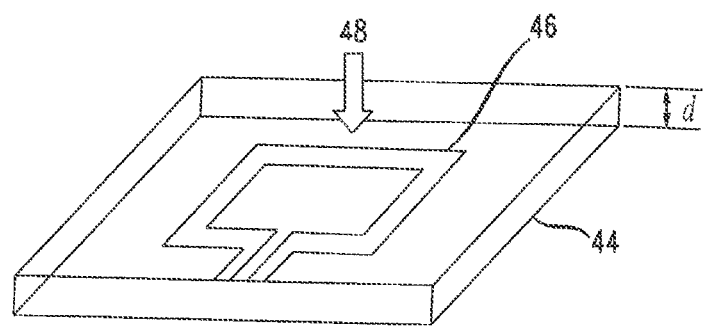
FIG. 4B illustrates a change in the distance between a top portion of a substrate on which a loop antenna sensor is placed and a bottom portion of the substrate due to pressure on the substrate.

As shown in FIG. 4B, when a pressure force is applied to the substrate, the loop antenna 46 is brought closer to the reflector 44. That is, the distance d between the sides of the substrate 42 decreases. This increases the capacitance of the resonant circuit and pushes the resonant frequency of the loop antenna towards a lower frequency, as shown in 4C which illustrates return loss as a function of resonant frequency.

Figure 4C:
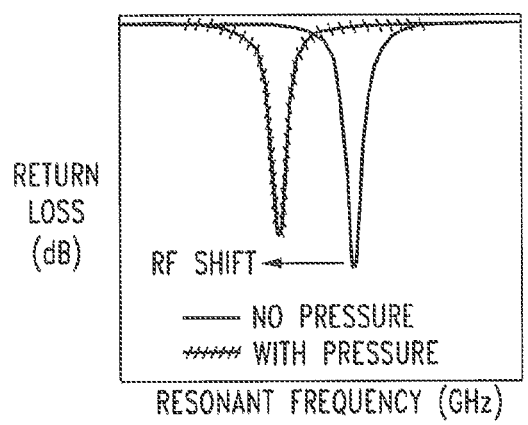
FIG. 4C illustrates an effect of pressure on a resonant frequency of a loop antenna.

The S11 curves of the loop antenna with and without pressure applied are shown in FIG. 4C. FIG. 4C shows the effect of pressure on the loop antenna frequency. The amount of frequency shift depends on the distance d between the reflector and the loop antenna. Therefore, the distance d can be quantitatively measured from the resonant frequency shift of the loop antenna, once the relationship between the distance d and the antenna resonant frequency shift is established.

Sensor Assembly FIG. 5

According to an illustrative embodiment, the shear and pressure sensors may be placed vertically inside a shoe to simultaneously measure shear and pressure at one point. The pressure sensor may be implemented by placing the loop antenna underneath the patch antenna, so that the antenna patch can serve as the reflector for the loop antenna. Based on implementation, the size of the loop has to be smaller than the size of the patch. In this case, we chose the diameter of the loop antenna sensor to be 13 mm. The resonant frequency of the loop antenna can then be calculated from the diameter a of the loop by:

$$f = c/\lambda = c/\pi a \quad (4)$$

where c is the velocity of light and λ is the microwave wavelength at the antenna resonant frequency, which is 6.5 GHz for a 13 mm loop antenna.

The radius b of the loop wire is then calculated from the aspect ratio Ω, i.e., $$\Omega = 2 \ln(2\pi a/b) \quad (5)$$

For a 13 mm loop antenna and an aspect ratio of 12, the radius of the loop wire was obtained as 0.25 mm.

Figure 5A:
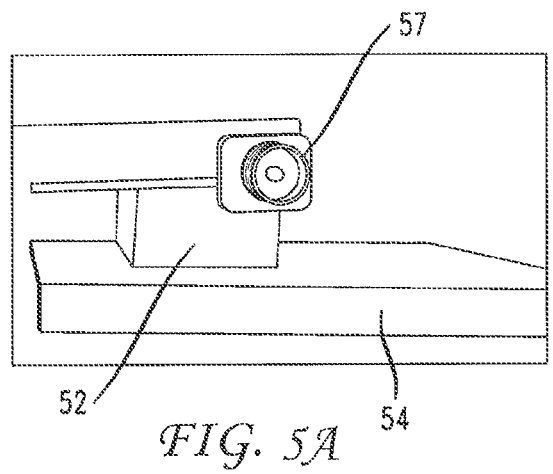
FIGS. 5A and 5B illustrate an example of fabrication of a patch antenna sensor.
Figure 5B:
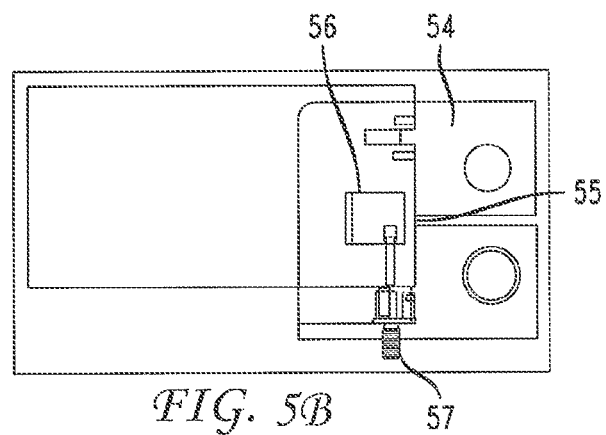
Figure 5C:
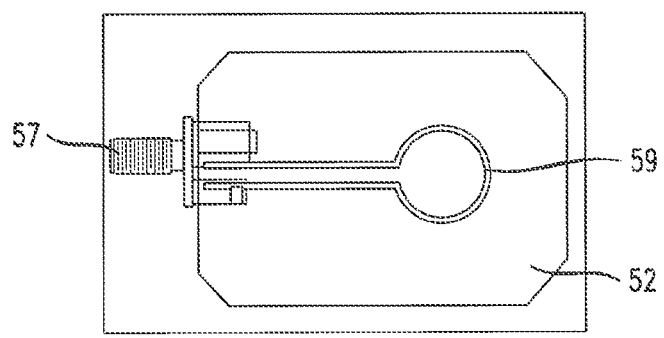
FIG. 5C illustrates an example of fabrication of a loop antenna sensor.

As an illustration of fabrication of a sensor assembly, reference is made to FIGS. 5A-5C which depicts an actual fabrication conducted for experimentation. Referring first to fabrication of the patch antenna sensor, the antenna sensor was fabricated on a laminate board with a dielectric constant c=3.66 and 35 μm thick copper films on both sides (Rogers 4350B). The laminate board was be cut into 50 mm long and 20 mm wide rectangular pieces, and the patch antenna sensor may replicated on one side of the laminate using press-n-peel PCB transfer film. The board was then dipped in a Ferric Chloride solution for ten to fifteen minutes to etch off the copper around the antenna sensor, followed by thoroughly rinsing the laminate in water and leaving it to dry completely. A pillar shaped Poron® substrate was then sandwiched between the sensor and the ground plane with a slot. In order to obtain a linear response of the sensor, the antenna sensor was placed parallel to the length direction of the patch with a slot/patch overlapping length of 9 mm, which is greater than 50% of the patch length.

Fabrication of the patch antenna sensor in this manner is illustrated in FIGS. 5A and 5B which depict a patch antenna 56 deposed on one side of a substrate 52, with a ground plane 54 with a slot 55 disposed on the other side. As shown in FIGS. 5B and 5B, a Subminiature Version A (SMA) connector 57 was mounted on the dielectric substrate 52 to facilitate the interrogation of the patch antenna sensor for experimentation. Although not illustrated, the patch antenna sensor assembly was then connected to a Vector Network Analyzer (VNA, Rohde & Schwarz, ZVA 24) through the SMA connector 57 to measure the S11 parameter of the antenna sensor.

The fabrication of the loop antenna sensor was accomplished following a similar press-and-peel PCB transfer method. FIG. 5C depicts a fabricated loop antenna which includes a loop 59 fabricated on a substrate 52 and connected to an SMA connector 57. The loop antenna sensor was connected via the SMA connector 57 to a VNA to measure the S11 parameter of the antenna sensor.

Patch Antenna Measurements FIG. 6

To test and calibrate the patch antenna sensor, controlled shear deformation was applied to the substrate via a plastic plate bonded on top of the antenna sensor. The displacement was applied along the direction that increases the overlapping length between the antenna sensor and a slot on an aluminum ground plane. The aluminum ground plane was fixed to an optical table and the plastic plate bonded on the antenna sensor was attached to a translation stage controlled by a DC servo controller (Thorlabs, TDC001). The servo controller was connected to a computer USB port. The translation stage connected to the controller was subjected to gradual lateral displacement and the controller was stopped at intervals of 0.5 mm so that the S11 parameter of the antenna sensor could be measured using a VNA. The measurement was conducted at each interval for a total shear displacement of 3 mm.

Figure 6A:
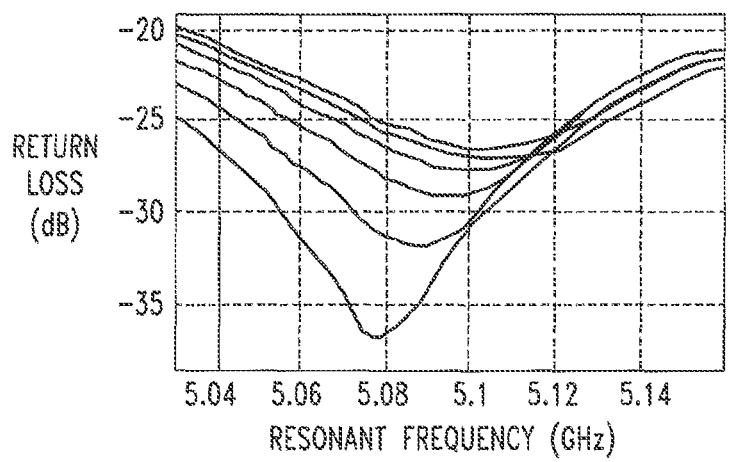
FIG. 6A illustrates graphically how a shear force on a patch antenna sensor causes shifts of S11 curves.

The S11 curves of the antenna sensor at different shear displacements are shown in FIG. 6A. The right most curve was measured when the overlapping length between the slot and the antenna sensor was 8 mm. Each subsequent shift of the curve to the left corresponds to a 0.5 mm increase in shear displacement. The left most curve represents the S11 curve of the antenna sensor when the shear displacement was 3 mm.

Figure 6B:
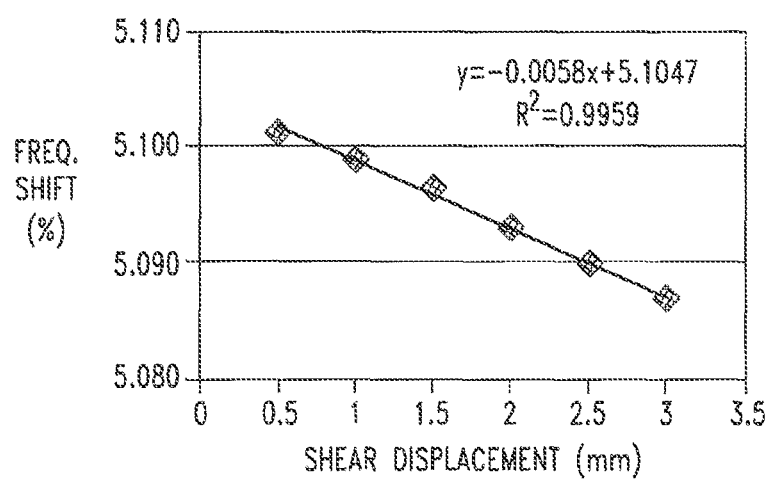
FIG. 6B illustrates graphically how a shear force affects a resonant frequency of a patch antenna.

Plotting of the $f_{10}$ frequencies of the antenna sensor obtained from the S11 curves versus the shear displacement is depicted in FIG. 6B. As can be seen from FIG. 6B, the $f_{10}$ frequency shifted linearly toward the lower frequencies with the increasing shear displacements. Based on the linear relationship between the $f_{10}$ frequencies and the shear displacement shown in FIG. 6B, the shear sensitivity of the antenna sensor was estimated to be 5.8 MHz/mm. Since the frequency resolution of the VNA was chosen as 0.2 MHz (10001 data points over a range of 2 GHz), the antenna sensor used in the experiment could detect shear displacement with a resolution of 34 μm. The shear forces acting over the patch antenna may be calculated from the shear deformation and material properties of the substrate. A plot such as that shown in FIG. 6B may be used as a calibration curve to determine lateral displacement of the substrate supporting a patch antenna.

Pressure Sensor Measurements FIG. 7

To test the pressure sensitivity of the loop antenna sensor, a Poron® substrate (6 mm thick) was sandwiched between the sensor and the reflector. The Poron substrate acted as a cushion which is compressed when pressure is applied on the reflector, thus bringing the reflector closer to the loop antenna sensor. The pressure on the reflector was applied with a closed-loop servo hydraulic mechanical tester. An additional layer of PDMS® substrate was placed below the antenna sensor to imitate the bottom sole of the shoe. To apply a uniform pressure distribution over the sensor surface, the sensor was placed between the two cylindrical bars (1 inch diameter, 6 inch long). Pressure was incrementally applied from 0 to 50 psi at intervals of 10 psi. The load was paused at each interval and the S11 parameters of the antenna sensor were measured on a VNA. To measure the hysteresis of the Poron® substrate, the measurements were repeated several times.

Figure 7A:
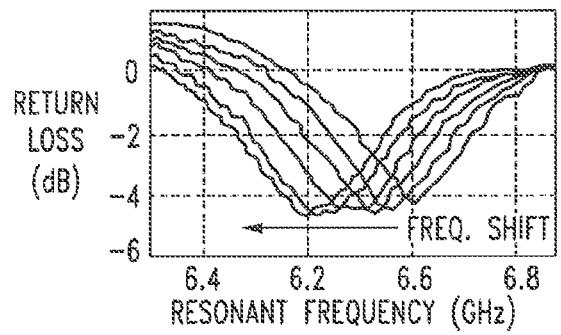
FIG. 7A illustrates graphically how pressure on a loop antenna sensor causes shifts of S11 curves.
Figure 7B:
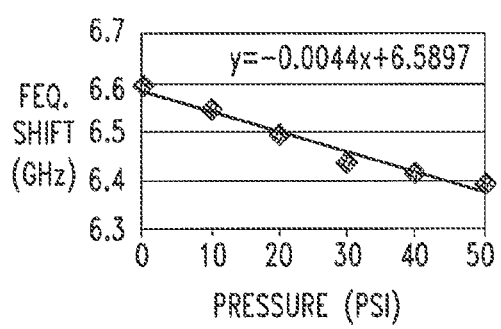
FIG. 7B illustrates graphically how pressure affects the resonant frequency of a loop antenna.

The S11 curves of the pressure antenna sensor at different pressure levels are shown in FIG. 7A. The right-most curve was measured when no pressure was applied over the reflector. Each subsequent curve represents the resonant frequency shift with a pressure increase of 10 psi. The resonant frequencies identified from the S11 curves were plotted vs. the applied pressure shown in FIG. 7B. The relationship is almost linear with a sensitivity of 4.4 MHz/psi. Assuming the resolution of VNA is 1 MHz (6000 data points over a range of 3 to 9 GHz), pressures as small as 0.25 psi can be effectively monitored with the loop antenna sensor. A plot such as that shown in FIG. 7B may be used as a calibration curve to determine vertical displacement of the substrate supporting a loop antenna.

Figure 7C:
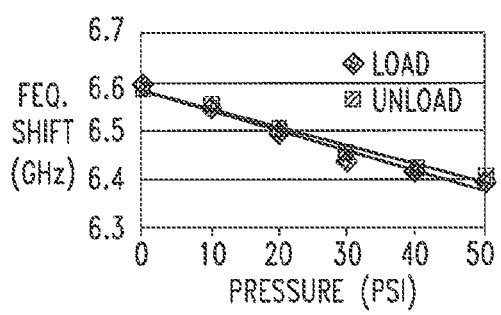
FIG. 7C illustrates hysteresis loss in a loop antenna sensor due to pressure.

The results from repeated loading cycles indicated that the hysteresis of the loop antenna sensor was below 0.2%, as shown in FIG. 7C.

Although the experiments described above used sensors connected to a VNA via an SMA connector, according to illustrative embodiments, the disclosure is not limited to wired interrogation of the sensors. The sensors may be wirelessly interrogated to measure shear force and pressure on a structure.

Sensor Assembly Simultaneous Measurements FIG. 8

Principles for simultaneous shear and pressure sensing, wireless interrogation, and sensor multiplexing are described below. It should be appreciated that various aspects of wireless interrogation and evaluation of sensor results, as described herein, may be executed by a computing device including a digital signal processor and a memory containing computer readable instructions executable by the digital signal processor.

Figure 8A:
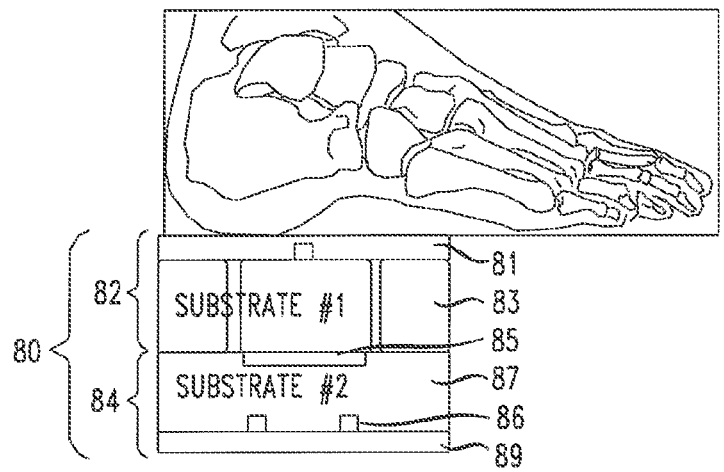
FIG. 8A illustrates a side view of sensor assembly for simultaneous sensing of shear force and pressure on an insole of a shoe according to an illustrative embodiment.

FIG. 8A illustrates a side view of a sensor assembly for simultaneously sensing shear and pressure according to an illustrative embodiment. For simultaneous shear and pressure sensing, the patch and loop antenna sensors described above may be stacked vertically to form a tri-axial force sensor assembly 80 as shown in FIG. 8A. Referring to FIG. 8A, a shear antenna sensor 82 may be placed directly under the foot, and a pressure sensor 84 may be placed underneath the shear antenna sensor. The shear antenna sensor 82 may be constructed from a ground plane 81 with two perpendicular slots, a first flexible dielectric substrate 83, and the antenna patch 85. The pressure sensor 84 may be formed by a loop antenna 86 and a second flexible dielectric substrate 87, with the antenna patch 85 serving as the reflector.

According to an illustrative embodiment, the slots on the ground plane 81 are not through-slots. Therefore, the antenna sensors are electrically isolated from the foot. A thin fabric can be laminated on top of the slotted ground plane 81 for user comfort. The loop antenna 86 may be backed with a rigid substrate with a copper coating 89 to eliminate the interferences from the ground.

Figure 8B:
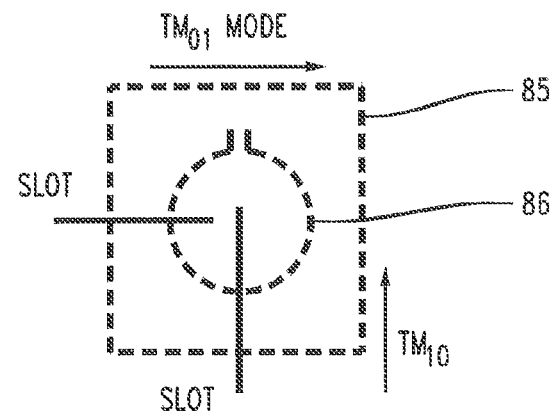
FIG. 8B illustrates a top view of the sensor assembly shown in FIG. 8A.

FIG. 8B illustrates a top view of the sensor assembly shown in FIG. 8A, including the antenna patch 85 and the loop antenna 86.

Interrogation Unit FIG. 9

Figure 9A:
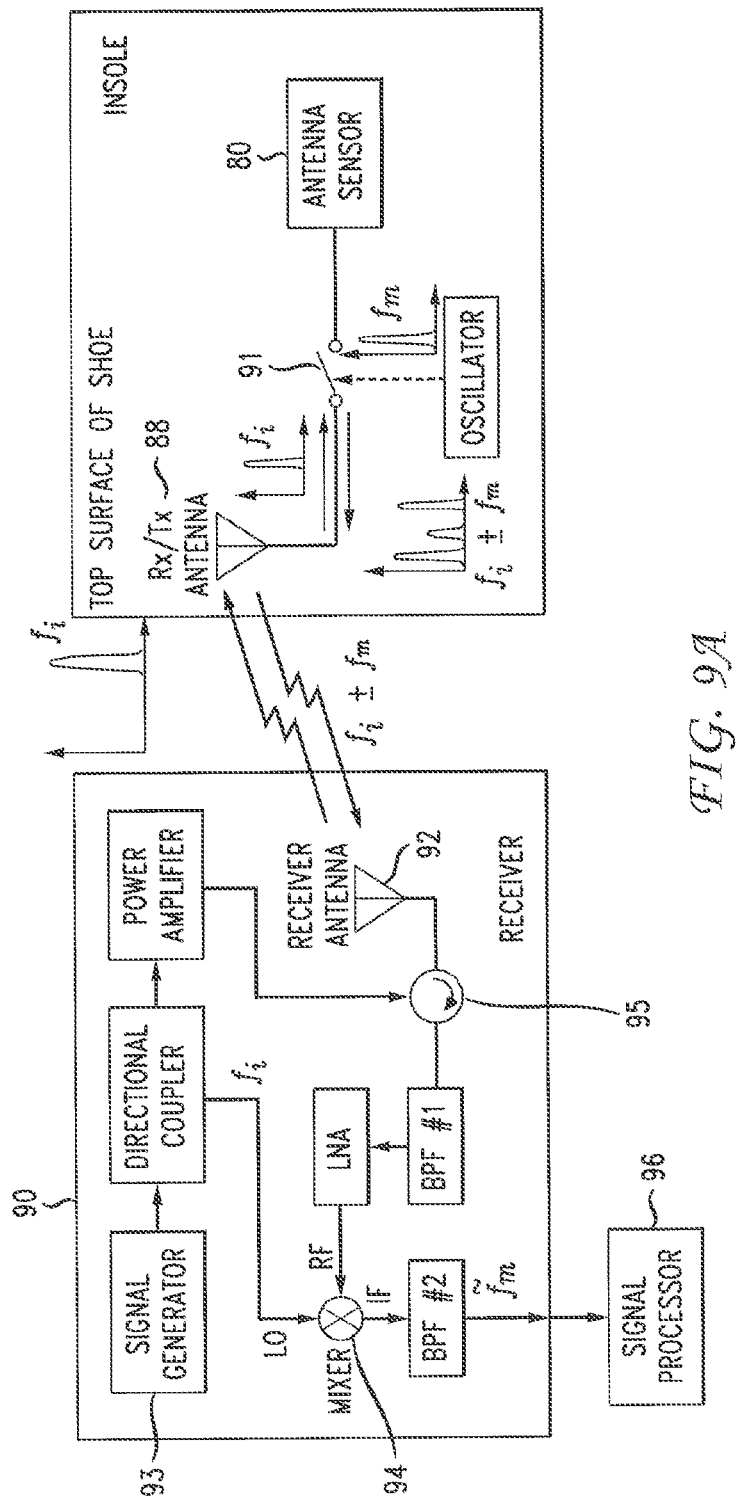
FIG. 9A illustrates a system for wireless interrogation of an antenna sensor assembly according to one illustrative aspect.

Wireless interrogation of the antenna sensor assembly may be conducted using a wireless interrogation unit, such as the wireless interrogation unit 90 shown in FIG. 9A. Referring to FIG. 9A, the antenna sensor assembly 80 formed on the insole of a shoe is connected to a broadband Rx/Tx 88 antenna through a microwave switch 91 on the top of the shoe. The interrogation signal $f_i$ is generated by a signal generator 93 in the wireless interrogation unit 90. As described in further detail below, the interrogation signal may be split into two parts by a direction coupler, amplified by a power amplifier, and directed to the Rx/Tx antenna 92 by a circulator 95.

The transmitted interrogation signal is received by the Rx/Tx antenna 88. The received interrogation signal may be either reflected by the switch 91 or by the antenna sensor 80, depending on the switch state. By controlling the switch 91 using an oscillator, the reflected signal is amplitude-modulated at the oscillator frequency $f_m$, i.e. the reflected signal has a modulated frequency of $f_i \pm f_m$. The amplitude of this modulation is determined by the antenna frequency. If $f_i$ matches the antenna frequency, the reflection from the antenna sensor is weak because the antenna radiates most of the signal. On the other hand, if $f_i$ is outside the bandwidth of the antenna sensor, the antenna reflection is strong due to its weak radiation. Therefore, the radiation characteristics of the antenna sensor are encoded in the amplitude-modulation of the reflected signal. This is described in more detail below with reference to FIGS. 10 and 12.

The reflected signal, re-radiated by the Rx/Tx antenna 88, is received by the receiver antenna 92, filtered by a band-pass filter (BPF #1) amplified by a low noise amplifier (LNA), mixed with other part of the interrogation signal from the signal generator 93 via a mixer 94, and then filtered again through another band-pass filter (BPF#2) to recover the modulation signal. The antenna resonant frequency can then be determined from the frequency-amplitude relationship of this demodulated signal $\hat{f}_m$ using, e.g., a signal processor 96. The signal processor 96 may include a digital signal processor, analog circuitry, and/or a combination of both.

On the sensor side, the Rx/Tx antenna 88, the switch 91, and the antenna sensor assembly 80 are passive components that do not need any power. The only component that needs external power is the oscillator, which consumes around 2-3 µW. Therefore, it is possible to power the oscillators using an energy harvesting device, such as a photocell. This wireless interrogation scheme may use discrete components.

Figure 9B:
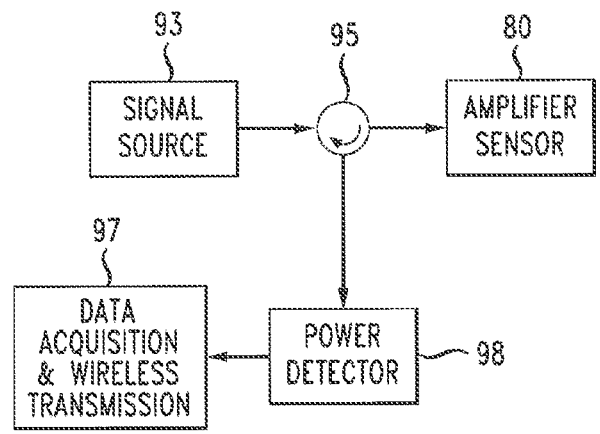
FIG. 9B illustrates a system for wireless interrogation of an antenna sensor assembly according to another illustrative aspect.
Figure 9C:
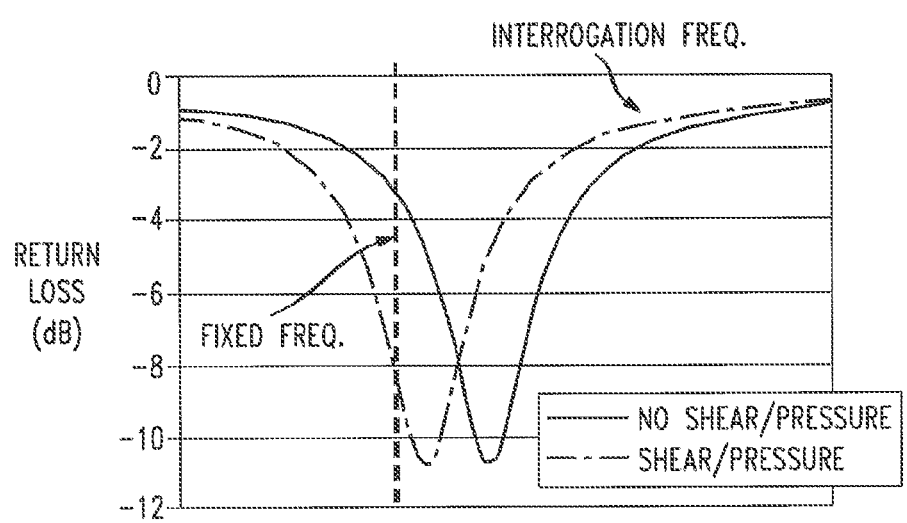
FIG. 9C illustrates graphically how a change in the resonant frequency shift of an antenna sensor causes a change in the reflected power for a fixed interrogation frequency.

Further aspects of wireless interrogation of the sensor are shown in FIGS. 9B and 9C. The signal generator 93 generates an interrogation signal with a fixed or swept frequency. This interrogation signal is routed toward the antenna sensor assembly 80 through a circulator 95.

The signal reflected by the antenna sensor assembly 80 is again routed by the circulator 95 to a Radio Frequency (RF) power detector, which produces a DC voltage output that is proportional to the power of the reflected signal. If the interrogation frequency is swept around a given frequency, the S11 curve of the antenna sensor can be constructed, from which the frequency shift of the antenna sensor can be determined. If the interrogation frequency is fixed, the resonant frequency shift of the antenna sensor will cause a change in the power of the reflected signal. This may be understood with reference to FIG. 9C which illustrates the return loss as a function of the resonant frequency.

A calibration process can establish the relationship between the voltage output of the power detector 98 and the resonant frequency shift of the antenna sensor assembly 80. The voltage output of the RF power detector 98 can be acquired using a conventional data acquisition device 97 and transmitted wirelessly using a wireless transponder.

To further illustrate aspects of wireless interrogation of an antenna sensor, reference is made to the detailed description of wireless sensor interrogation of a microstrip patch antenna below. Although this description to a microstrip patch antenna, it should be appreciated that a sensor including a microstrip patch antenna and a loop antenna may be wirelessly interrogated in a similar manner. For further details of wireless interrogation of a sensor, the reader is directed to "Battery-less wireless interrogation of microstrip patch antenna for strain sensing", by X. Xu and H. Huang, Smart Materials and Structures, Oct. 31, 2012, herein incorporated by reference.

When an interrogation signal is transmitted to an antenna, the antenna will receive the signal if the interrogation signal falls within its operation frequency band, and the antenna will reflect the signal out of its operation frequency band. Assuming the antenna is not terminated with a 50Ω load, the received signal will be reflected at the antenna termination and re-radiated by the antenna. This re-radiated signal is referred to as antenna backscattering. Therefore, by sweeping the interrogation frequency, the antenna resonant frequency can be identified as the interrogation frequency at which the antenna backscattering is the strongest.

Unfortunately, the structures surrounding the antenna also reflect the interrogation signal and thus create structural backscattering. This structural backscattering is independent of the antenna resonant frequency. In general, the strength of the structural backscattering is several orders of magnitude higher than that of the antenna backscattering. As a result, the antenna backscattering is 'buried' inside the structural backscattering, causing the well-known 'self-jamming' problem.

Figure 10:
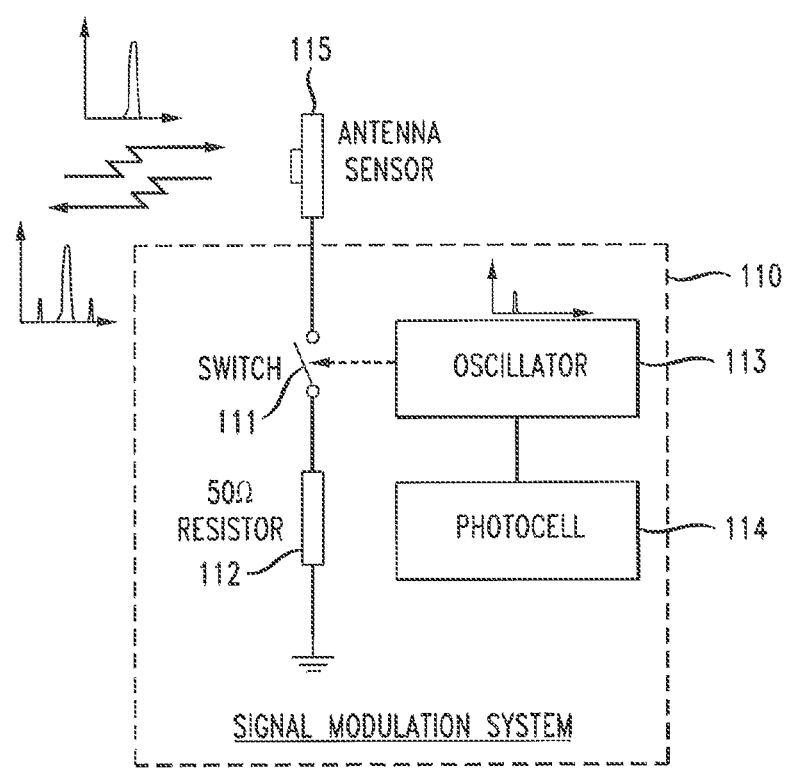
FIG. 10 illustrates another view of an antenna sensor assembly according to an illustrative embodiment.
Figure 11A:
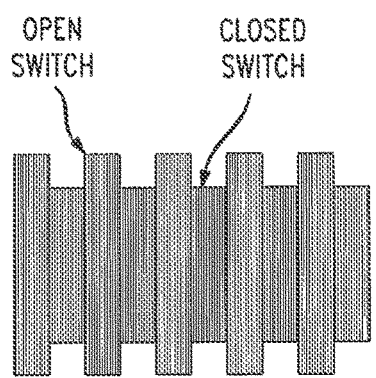
FIGS. 11A and 11B illustrate a time domain representation of a backscattered signal when an interrogation frequency is close to an antenna sensor resonant frequency and away from the antenna sensor resonant frequency, respectively.
Figure 11B:
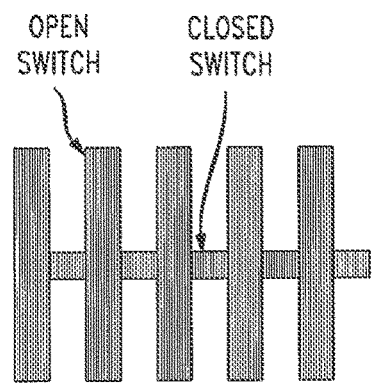
Figure 11C:
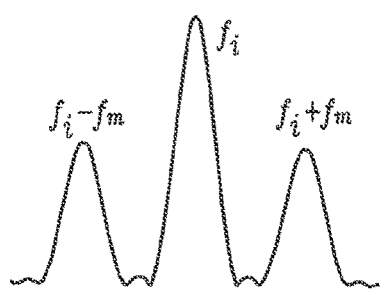
FIGS. 11C and 11D illustrate a frequency domain representation of a backscattered signal when an interrogation frequency is close to an antenna sensor resonant frequency and away from the antenna sensor resonant frequency, respectively.
Figure 11D:
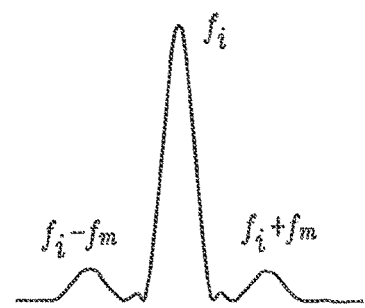
Figure 12:
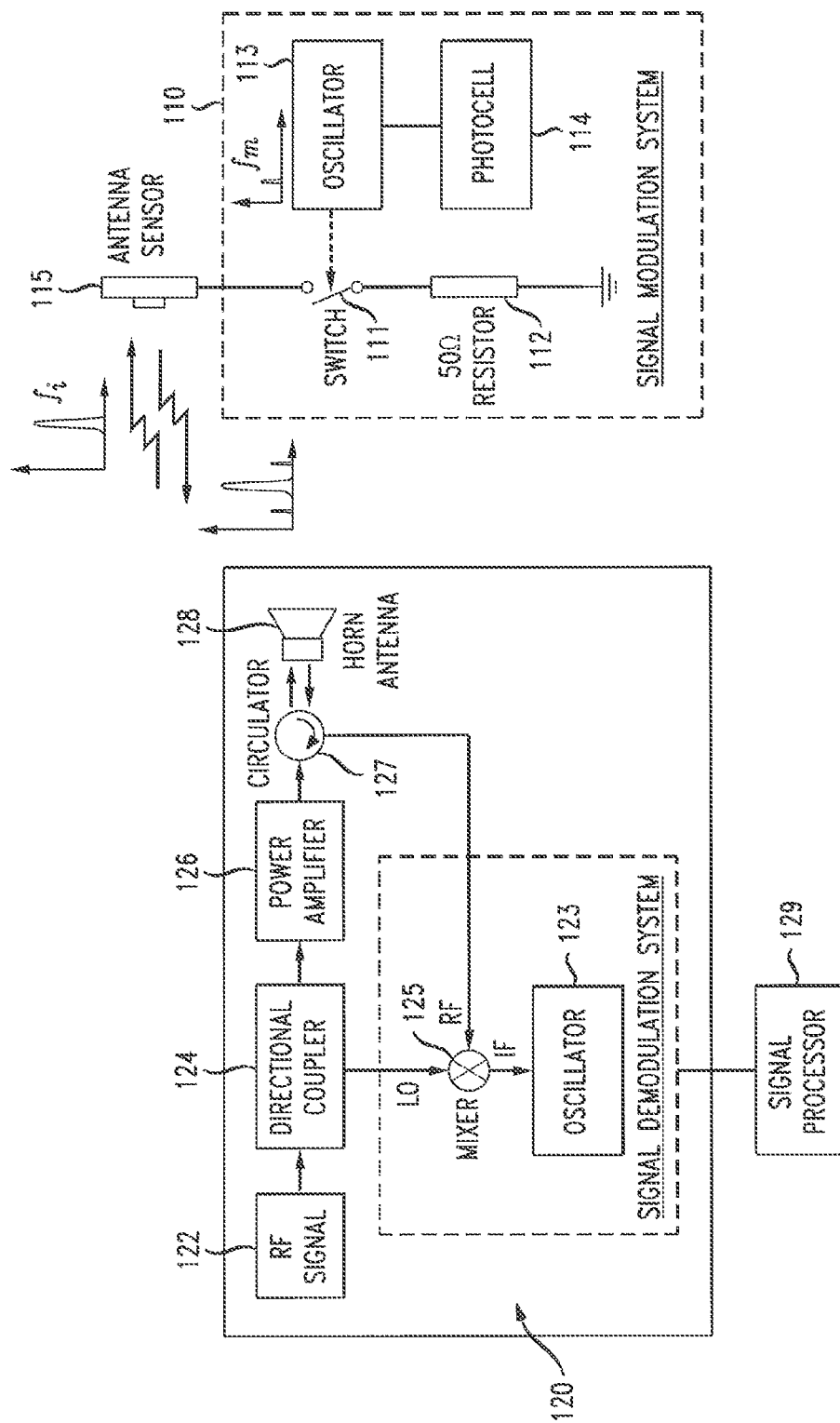
FIG. 12 illustrates an alternative view of a system for wirelessly interrogating an antenna sensor assembly according to an illustrative embodiment.

Signal Modulation System FIGS. 10-12

According to an illustrative embodiment, an amplitude modulation scheme may be used to isolate the antenna backscattering from the structural backscattering. This may be understood with reference to FIG. 10 which illustrates an amplitude or signal modulation system 110 for isolating antenna backscattering from structural backscattering.

The amplitude modulation system 110 includes a switch 111 that switches the termination of the antenna sensor 115 (which may be the same as the antenna sensor assembly 80) from open-to-ground to a 50Ω resistor 112. The impedance switching is controlled by an oscillator 113 powered by, e.g., a photocell 114. When the switch 111 is open, all the received signal from the antenna sensor 115 is reflected by the switch, thus generating a large antenna backscattering. When the switch 111 is closed, the received signal is dissipated by the 50Ω resistor 112 and thus results in little or no antenna backscattering. In other words, the amplitude of the antenna backscattering is modulated by the switching states of the switch 111.

Controlling the switch 111 using the output of the oscillator 113, therefore, causes amplitude modulated backscattered signals such as those shown in FIG. 11A or 11B to be generated. FIG. 11A illustrates a time domain representation of the backscattered signal when the interrogation frequency is close to the antenna resonant frequency, and FIG. 11B illustrates a time domain representation of the backscattered signal when the interrogation frequency is away from the antenna resonant frequency. Assuming the oscillator 113 has a frequency of $f_m$, the frequency of the amplitude modulated backscattered signal $f_{BS}$ is then:

$$f_{BS} = f_i \pm f_m \qquad (6)$$

In other words, these amplitude modulated signals have frequency sidebands that are offset from the interrogation frequency $f_i$. This may be understood with reference to FIGS. 11C and 11D which illustrate a frequency domain representation of the backscattered signal when the interrogation frequency is close to and away from the antenna resonant frequency, respectively. Due to the frequency offset, these sidebands can be easily isolated from the structural backscattering since the structure backscattering has the same frequency as the interrogation frequency. The amplitudes of the sidebands are governed by the interrogation frequency as well as the antenna resonant frequency.

If the interrogation frequency $f_i$ matches the antenna resonant frequency, most of the energy imposed on the antenna will be received by the antenna and dissipated by the 50Ω load when the switch 111 is closed. This leads to a large difference in the amplitudes of the backscattered signal at the two switching states, producing sidebands with large amplitudes as shown in FIGS. 11A and 11C. If the interrogation frequency is far from the antenna resonant frequency, the signal received by the antenna will be small. As a result, the amplitudes of the antenna backscattering will have a small difference for the two switching states, i.e., the side bands will small amplitudes, as shown in FIGS. 11B and 11D. Therefore, the antenna resonant frequency can be identified as the interrogation frequency at which the amplitude of sidebands is the maximum.

Since the switch 111 and the antenna sensor 115 are passive components, they do not need any power to operate. The only component that needs external power is the oscillator 113. By employing an oscillator 113 that consumes only a few microwatts, it is possible to operate the sensor node using a solar-cell based energy harvesting device, e.g., the photocell 114.

The generation of the interrogation signal and the recovery of the sidebands can be carried out by a wireless sensor interrogation unit (WSIU) 120 illustrated in FIG. 12. As shown in FIG. 12, the signal generated by an RF source 122 is split into two parts by a directional coupler 124. One part of the signal is amplified by a power amplifier 126 and routed to an antenna, such as a horn antenna 128, through a circulator 127. Broadcast by the horn antenna 128, this signal serves as the interrogation signal for the unpowered wireless antenna sensor 115.

The recovery of the sidebands from the backscattered signal is based on the principle of frequency conversion. The backscattered signal is first received by the horn antenna 128 and directed to the RF port of a mixer 125 by the circulator 127. The mixer 125 also receives the other part of the signal generated by the RF source 122 at its local oscillator (LO) port. As a result, the mixer 125 produces an intermediate frequency (IF) signal:

$$\tilde{f}_m = fBS \pm fi = fm \text{ and } 2fi \pm fm \qquad (7)$$

After removing the high-frequency component $2f_i \pm f_m$ using a low-pass filter, such as the BPF#2 shown in FIG. 9A, a demodulated signal $\tilde{f}_m$ can be recovered at the filter output and can be acquired by an oscilloscope 123. Since the amplitude of the demodulated signal $\tilde{f}_m$ is proportional to the sidebands, the antenna resonant frequency can be determined from the frequency-amplitude relationship of the demodulated signal $\tilde{f}_m$ using, e.g., a signal processor 129. The signal processor 129 may include a digital signal processor, analog circuitry, and/or a combination of both.

Figure 13:
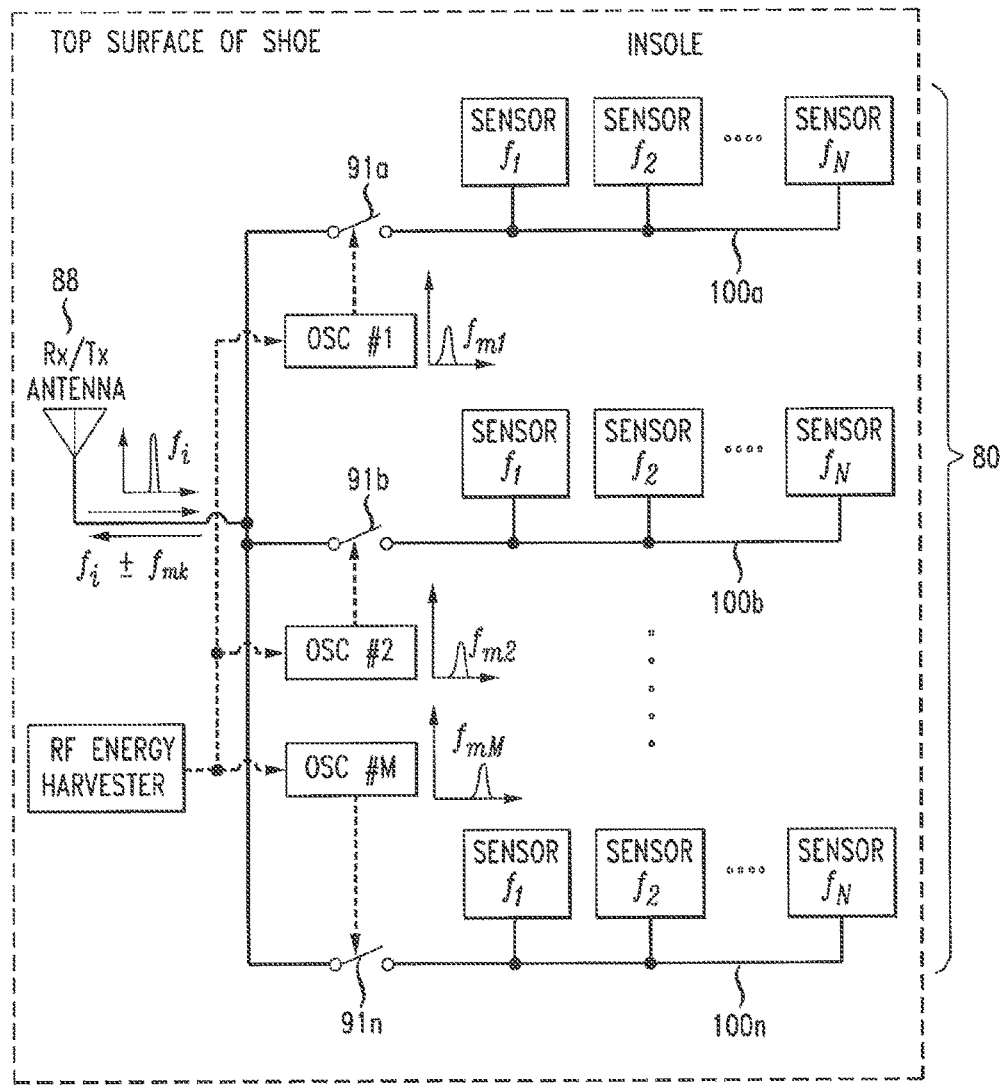
FIG. 13 illustrates a sensor assembly with multiple sensors employing frequency division multiplexing according to an illustrative embodiment.
Figure 14:
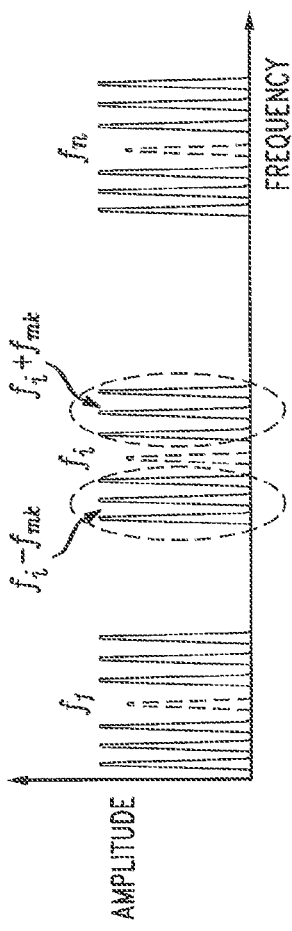
FIG. 14 illustrates a frequency spectrum of a signal received from a sensor assembly, such as that shown in FIG. 13.

Array of Sensors FIGS. 13-14

Referring again to the shear and pressure antenna sensors, to map the shear and pressure distribution, a large number of sensors n may be distributed in the insole as part of the sensor assembly 80, as depicted in FIG. 13. To acquire the data from these sensors without noticeable latency, two frequency division multiplexing schemes may be used.

First, multiple antenna sensors n, each operating with a designated narrow frequency band, may be implemented to share the interrogation frequency band. These antenna sensors may be connected through a single microstrip transmission line (100 a, 100 b, ... 100 m) and controlled by one oscillator-switch (91 a, 91 b, ... 91 m, respectively). Secondly, the oscillator/antennas configurations can be repeated by varying the oscillator frequencies for each antenna sensor group.

As a result, the re-radiated signal has a frequency spectrum shown in FIG. 14, in which the modulated signal from a particular antenna sensor occupies unique frequencies $f_i \pm f_{mk}$. Assuming that there are M oscillators, each controlling N antenna sensors, simultaneous interrogation of M×N sensors can be achieved.

For testing purposes, a shoe was instrumented with one set of shear and pressure sensors. The insole of a regular shoe was cut out, and the antenna sensors fabricated on a foam material (Poron Urethane Foam, Rogers Corporation) were placed inside the cut-out portion of the shoe. The antenna sensors and the transmission lines were fabricated from a copper film bonded on a flexible Kapton film using a "Press-n-Peel" etching technique. The transmission lines were routed to the top of the shoe and connected to the antenna sensors.

RF sources were used to generate the interrogation signals, and circulators were introduced to route the signals reflected by the antenna sensors to an Arduino board, which acquired the sensor output and transmitted the data wirelessly using an Xbee wireless module. Preferably, the sensor signal should be amplified before the data acquisition. Using a wireless receiver, the in-shoe sensor circuitry may be drastically reduced. In addition, an entire shoe may be fabricated instead of retro-fitting a regular shoe. These two improvements will increase the number of sensors that can be embedded in the insole without increasing the weight of the shoe.

The design of a smart shoe as described herein will start with the selection of sensor location and the number of sensors. At first, only a few sensors may be embedded at the locations that are more susceptible to ulceration. More sensors with smaller sizes may be added so that the plantar shear and pressure distribution during walking can be "mapped" out with the desired resolution.

The smart shoe may be fabricated on multi-layers of flexible sheets using a vacuum-assisted layer by layer lamination technique. The antenna and transmission line patterns can be first machined out of thin copper films using laser machining, precision milling, or chemical etching techniques.

According to an illustrative embodiment, and referring back to FIG. 8A, the fabrication process may start with bonding substrate #1 on a copper film with slots machined at the designed locations. Trenches may be milled off substrate #1 to form individual pillars. Next, the patch antenna, the transmission lines, and the Rx/Tx antenna (e.g. a microstrip ultra-wide-band antenna) may be laser machined from a copper film and transferred to a Kapton film. Heat activated adhesives can be applied on the Kapton or copper film surface by spray coating or stamping. This subassembly may then be glued on top of substrate #1 with the slots and the antenna patch properly aligned. The Rx/Tx antenna portion of the Kapton film may be wrapped around the substrate to form the shoe surface. The loop antenna for pressure sensing can be fabricated following the same procedure. The switch and the oscillator may be rigidly glued on the Kapton film and connected to the transmission lines using conductive epoxy.

The insole of the shoe can be built up layer by layer to ensure precision alignment of the sensor patterns. Vertical via holes filled with conductive epoxy can be used to provide electric connections between the two sensor layers. Following the lay-up process, the sensor package will be placed in a vacuum bag so that controlled pressure can be applied to ensure uniform bonding. The final curing of the adhesives may be activated by placing the vacuum bag in an oven with pre-selected temperature and curing time. Finally, the bottom of the shoe may be casted using a silicone rubber material to encapsulate the sensor nodes. The top surface of the shoe can be laminated with fabrics and Velcro strips to secure the shoe on the foot. The in-shoe sensors may be either powered by a Radio Frequency (RF) energy harvester or a small battery.

Once the functionality of the wireless receiver is confirmed, the entire receiver may be implemented on a printed circuit board so that it is small and light enough to be stored in a waist pouch.

Figure 15:
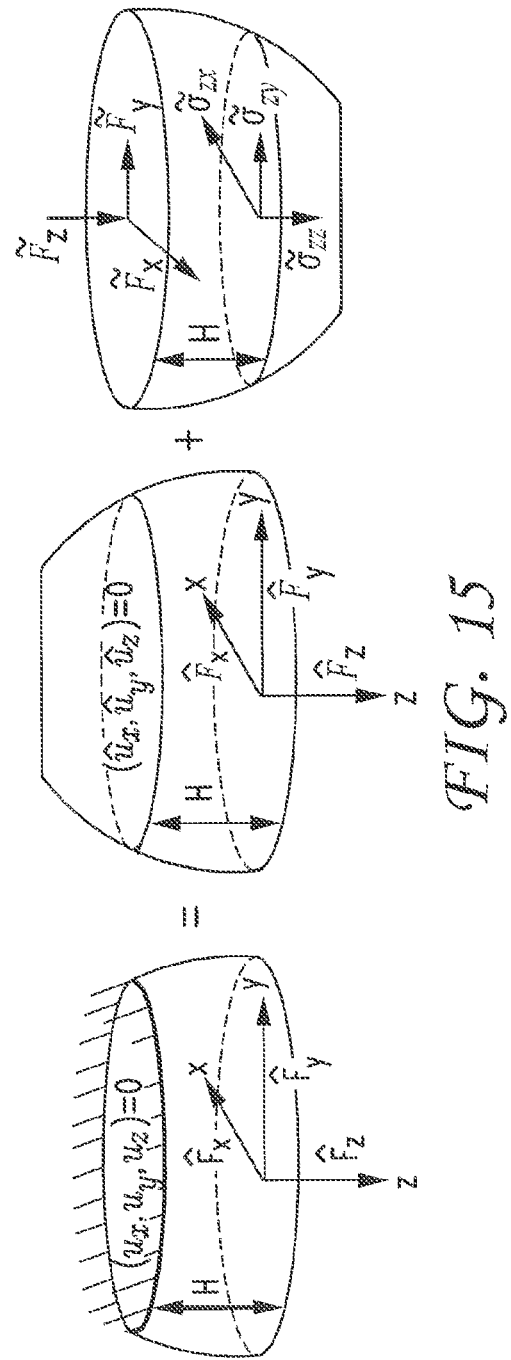
FIG. 15 illustrates how a semi-analytical biomechanics model may be used to calculate the internal stresses on a foot from collected antenna sensor data on a shoe worn by the foot according to an illustrative embodiment.

Biomechanics Model FIG. 15

Since internal stress, especially the stresses at the bone and tissue interface, may play an important role in developing ulceration, a semi-analytical biomechanics model may be used to calculate the internal stresses from the collected sensor data. This simulation model is intended for data processing at a foot clinic or using a portable single-board computer carried by a patient.

The plantar tissue layer may be simulated as an infinite plate with a finite thickness, as shown in FIG. 15. The bottom surface, representing the foot-insole interface, is subjected to three traction forces at each location while the top surface, representing the tissue-bone interface, is assumed to have fixed boundary conditions. The model can be treated as the superposition of two half-planes. The first half plane is subjected to the traction forces $(\hat{F}_x, \hat{F}_y, \hat{F}_z)$ at the XOY plane (where O is the origin) whose analytical solution, i.e. the Green's function, is known. The displacement $(\hat{u}_x, \hat{u}_y, \hat{u}_z)$ at any point on the plane coinciding with the tissue-bone interface can therefore be calculated by numerical integration of the Green's functions with the distributed traction forces $(\hat{F}_x, \hat{F}_y, \hat{F}_z)$. The 2nd half-plane is subjected to traction forces $(\tilde{F}_x, \tilde{F}_y, \tilde{F}_z)$ that generate displacements $(\tilde{u}_x, \tilde{u}_y, \tilde{u}_z)$ on the top surface and the stresses $(\sigma_{zx}, \sigma_{zy}, \sigma_{zz})$ on the bottom surface. The unknown traction forces, $(\hat{F}_x, \hat{F}_y, \hat{F}_z)$ and $(\tilde{F}_x, \tilde{F}_y, \tilde{F}_z)$, may be determined from the measured shear and pressure forces, i.e. $\hat{F}_i(x,y,0)+\int_s \sigma_{zi}(x,y,0)ds=F_i(x,y,0)$ and from the boundary condition $\hat{u}_i+\tilde{u}_i=0$ on the tissue-bone interface, where i=x, y and z. The stresses at any arbitrary points inside the finite strip can then be calculated from the summation of the stresses generated by $(\hat{F}_x, \hat{F}_y, \hat{F}_z)$ and $(\tilde{F}_x, \tilde{F}_y, \tilde{F}_z)$.

The plantar tissue may be assumed to be homogenous, isotropic, and linearly elastic. The material properties of the plantar tissue may be taken from previous studies. The internal stress indices (e.g. von Mises stress, maximum shear stress, maximum strain, etc.) at different distances from the bone-tissue interface may be presented in color maps to highlight the "high-risk" regions. The bio-mechanics model may be validated with finite element simulation results.

The smart shoe may be evaluated to understand clinical needs at two stages. The in-vivo 3D distributions of various stress/strain indices as well as their time-integrations, calculated from the data measured using shoes with a few sensors, may be analyzed to determine the number of sensors and the spatial resolution needed for the two intended applications, i.e. as a rehabilitation device or as a research tool. In addition, the ease-of-use and the graphic representation of the measurement and simulation results will also be evaluated. Based on the evaluation results, the design of the smart shoe, the wireless receiver, the simulation tool, and the graphic interfaces may be optimized. The portable wireless receiver and the smart shoes embedded with a higher number of sensors may be tested, and the results may be analyzed to correlate the measurement and simulation results to the existing clinical data and understandings. The comfort of wearing the entire system during walking may also be evaluated.

To meet the power requirement of the sensor identification circuit, the ultra-low power silicon oscillator that consumes about 2-3 µW (Touchstone semiconductor TS3002) may be used. It is estimated that the RF energy harvester should be able to harvest at least 1 mW DC power from the interrogation signal, which is sufficient to power more than 300 oscillators. However, the RF energy harvester might be too large to be accommodated on the shoe surface. If this is the case, a rechargeable Polymer Lithium Ion Battery (Spark fun PRT-00731, 5.7×12×28 mm, weight: 2.65 gram) may be used. A battery rated with nominal output of 3.7 V and a capacity of 110 mAh may be able to power ten of the 3 µW oscillator for more than 13,500 hours. The battery can be housed in the heel of the smart shoe.

As a rehabilitation device, only a few sensors distributed at the strategic locations are needed. In this case, the wireless sensor data can be acquired and processed using a single board computer (e.g. Digi SBC LP3500 Series). Other devices, such as a wireless watch (e.g. Texas Instrument eZ430-Chronos) can be used to provide the user interface. As a research tool, however, more sensors may be needed to provide sufficient sensor coverage and spatial resolution. In addition, the clinicians may also want to observe the measurements while the subject is walking.

A more powerful computer, such as a lightweight laptop or other computing device may be used to collect, process, and wirelessly transmit data. One skilled in the art will appreciate that such a device may include a processor, a memory, and a computer readable storage device upon which instructions are recorded which, when executed by the processor, cause the processor to perform collecting, processing, and wirelessly transmitting/receiving data. An alternative is to implement analog data processing circuitry so that high speed data processing can be achieved.

Figure 16:
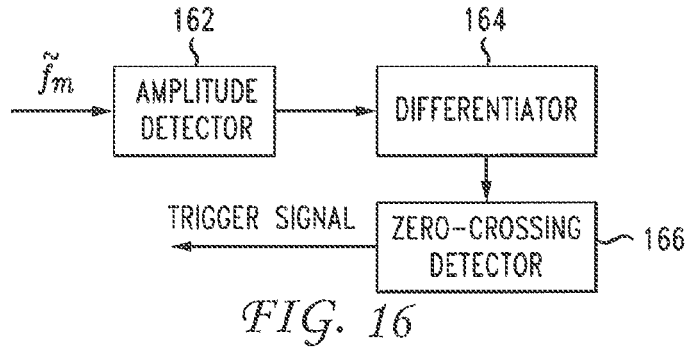
FIG. 16 illustrates an analog data processing circuit for processing signals received from an antenna sensor assembly according to an illustrative embodiment.

Data Processing FIG. 16

As shown in FIG. 16, the amplitude of the demodulated signal may be first detected by an amplitude detector 162, which outputs a signal whose maxima correspond to the antenna frequencies. This signal can then be passed through a differentiator 164 to convert the maxima to zero-crossings. At each zero-crossing, the zero-crossing detector 166 generates a trigger signal, based on which the resonant frequency of the corresponding antenna sensor can be determined. As a result, only one sample is collected from each antenna sensor for one frequency scan. This data can then be acquired using a low speed data acquisition card and wirelessly streamed to a computer for graphic display of the measurement data.

Figure 17:
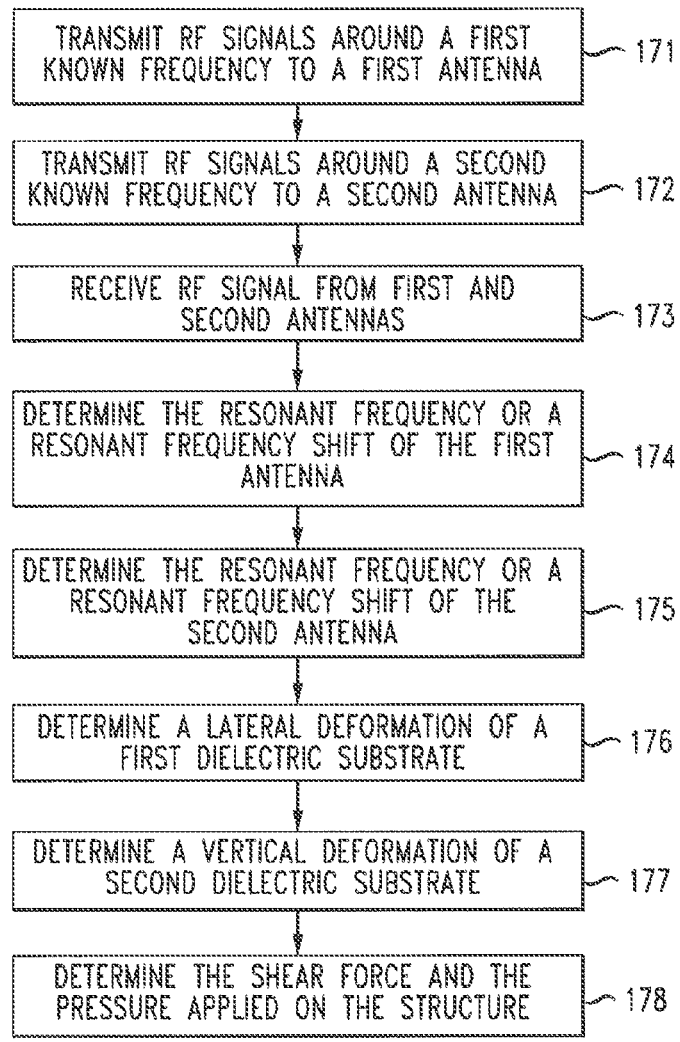
FIG. 17 illustrates a method for monitoring shear force and pressure on a structure according to an illustrative embodiment.

Method FIG. 17

FIG. 17 illustrates a method for monitoring shear force and pressure on a structure according to an illustrative embodiment. It should be understood that the steps or other interactions of the illustrated methods are not necessarily presented in any particular order and that performance of some or all the steps in an alternative order is possible and is contemplated. The steps have been presented in the demonstrated order for ease of description and illustration. Steps can be added, omitted and/or performed simultaneously without departing from the scope of the appended claims. It should also be understood that the method can be ended at any time. In certain embodiments, some or all steps of the method, and/or substantially equivalent steps can be performed by execution of computer-executable instructions stored or included on a non-transitory computer-readable medium.

Referring to FIG. 17, the method begins at step 171 at which RF signals having frequencies around a first known frequency are transmitted to a first antenna, e.g., a patch antenna sensor 82 including a radiation element 85 disposed on a first dielectric substrate 83 disposed on a second substrate 87. At step 172, RF signals having frequencies around a second known frequency are transmitted to a second antenna, e.g., a loop antenna sensor 84 including a radiation element supported by a second dielectric substrate. The RF signals may be transmitted by a transceiver included in the wireless interrogation units 90 and/or 120. At step 173, signals are received from the first and second antenna sensors by the wireless interrogation units 90 and/or 120. At step 174, the resonant frequency or a resonant frequency shift of the first antenna is determined, and at step 175, the resonant frequency or a resonant frequency shift of the second antenna is determined. At step 176, a lateral deformation of the first dielectric substrate is determined based on the determined resonant frequency shift of the first antenna or by comparing the determined resonant frequency of the first antenna and the first known frequency. At step 177, a vertical deformation of the second dielectric substrate is determined based on the determined resonant frequency shift of the second antenna or by comparing the determined resonant frequency of the second antenna and the second known frequency. At step 178, the shear force applied on the structure is determined based on the determined lateral deformation, and the pressure applied on the structure is determined based on the vertical deformation It should be appreciated that one or more of steps 174-178 may be performed by a digital signal processor, analog circuitry, or a combination of both.

Sensor with Reflector FIG. 18

Figure 18A:
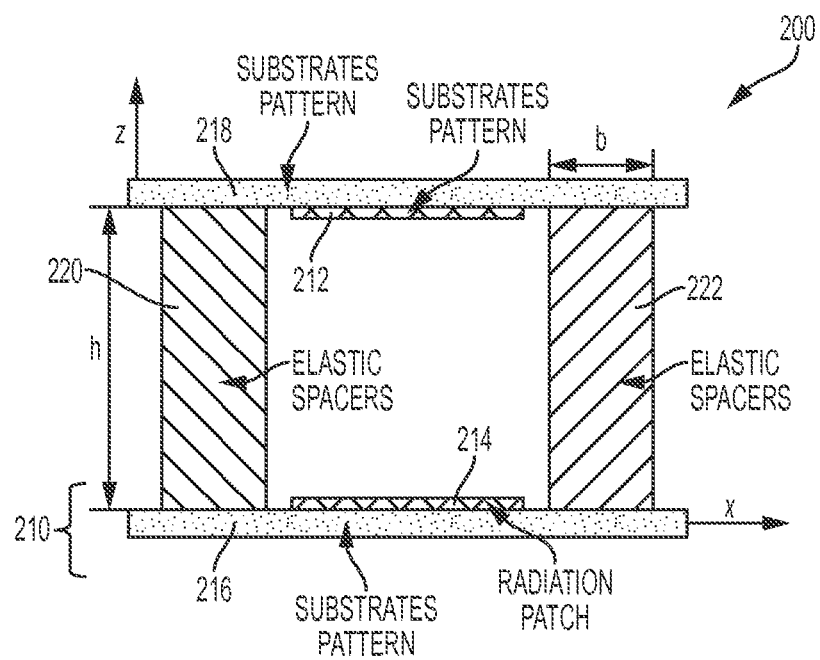
FIG. 18A illustrates an end view of a schematic of an antenna sensor including a reflector and a radiation patch according to an illustrative embodiment.
Figure 18B:
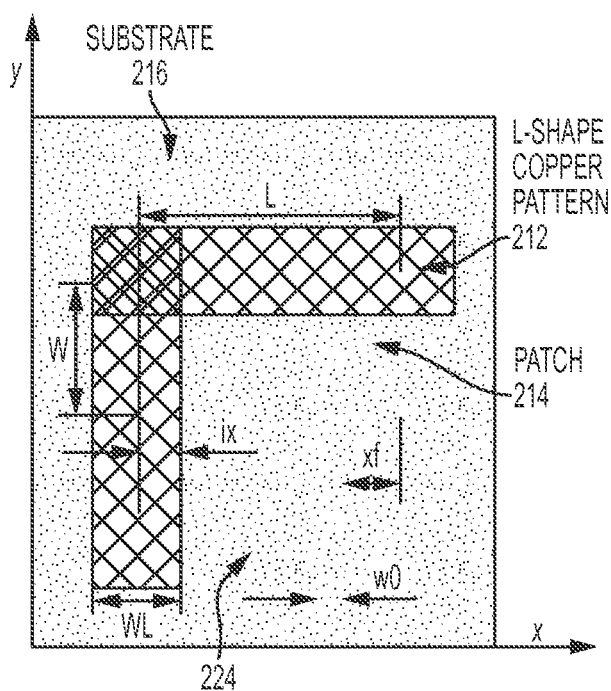
FIG. 18B illustrates a plan view of a schematic of the antenna sensor of FIG. 18A.

Referring to FIGS. 18a and 18b, another embodiment of a sensor 200 that demonstrates high sensitivity and linearity for both shear and pressure is now described. The sensor provides simultaneous measurement of shear stress and normal pressure with high sensitivity and spatial resolution.

The measurement of the sensor 200 is based on electromagnetic interference between a microstrip patch antenna 210 and a reflector 212 (e.g. a printed metallic pattern that defines a slot). The patch antenna 210 includes a radiation patch 214 on a substrate 216. The reflector 212 is located at a distance (e.g., height h) above a radiation patch 214 of the patch antenna 210. The metallic reflector 212 is attached to (e.g., inserted into) a substrate 218.

The metallic reflector 212 is separated from the radiation patch 214 by elastic spacers 220, 222. The elastic spacers 220, 222 have a height h and a width b. The thickness (not shown) of the spacers 220, 222 (e.g., as measured in the y-direction in FIG. 18b) should be sufficient so as to prevent the shear deformation in the y-direction.

In general, the reflector 212 has a shape that defines a slot 224. The metallic reflector 212 shown in FIG. 18b has an L-shape that covers two perpendicular edges of the radiation patch 214 with the slot 224 positioned over the other edges of the radiation patch 214. In the absence of a reflector 212, resonant frequencies of the patch antenna 210 are determined by the dimensions of the radiation patch 214 (i.e. L and W shown in FIG. 18b) as well as the dielectric constant of the substrate 216. When the metallic reflector 212 is placed above (i.e., spaced apart from) the patch antenna 210, an electromagnetic wave radiated by the patch antenna 210 is reflected by the reflector 212. The reflected electromagnetic wave interferes with the electromagnetic field radiated by the radiation patch 214, and changes the resonant frequencies of the patch antenna 210.

Further, a reflected electromagnetic wave is based on to the lateral and vertical position of the metallic reflector 212 with respect to the radiation patch 214. Because a change in the reflected electromagnetic wave changes how the reflected electromagnetic wave interferes with the electromagnetic field radiated by the radiation patch 214 of the antenna 210, the resonant frequencies of the antenna 210 are based on the lateral and vertical position of the metallic reflector 212 with respect to the radiation patch 214.

A shear force will bend the elastic spacers 220, 222 in the x-direction to change the lateral position of the reflector 212 with respect to the radiation patch 214 and a normal pressure will compress the elastic spacers 220, 222 (i.e., in the z-direction) to reduce the distance (e.g., height h) between the metallic reflector 212 and the radiation patch 214. As such, each an applied shear force and normal pressure causes a change in the resonant frequencies of the antenna 210 and, by monitoring the antenna resonant frequencies, shear forces and normal pressure on the sensor 200 can be detected.

Sensor Measurements FIGS. 19-20

Referring to FIGS. 19a, 19b, 19c, 19d, changes in resonant frequencies of antenna 210 in response to changes in lateral and vertical position of the reflector 212 are illustrated. Here, the resonant frequencies of antenna 210 are measured as the frequencies at which an S11 curve has a local minimum.

Shear displacement δx was introduced by translating the L-shape reflector 212 in the x-direction and normal pressure was introduced by placing the reflector 212 at different height distances (h) from the radiation patch 214. The height distances (h) in FIGS. 19a, 19b, 19c, 19d, are h=3.5 mm, 3.25 mm, 3.0 mm, 2.75 mm, and 2.5 mm, and the displacements (δx) are in increments of 0.5 mm, starting at x=0 mm and stopping at x=2 mm. At each combination of height and displacement, an S11 curve was collected. The initial position of the reflector 212 (e.g., x=0 mm and h=3.5 mm) represents a load free state.

Figure 19A:
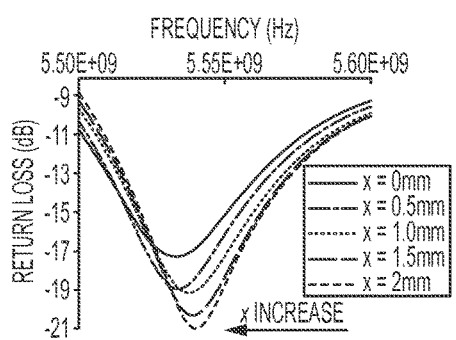
FIG. 19A illustrates graphically an effect of lateral displacement of the reflector on a first resonant frequency of the antenna sensor of FIG. 18A.
Figure 19B:
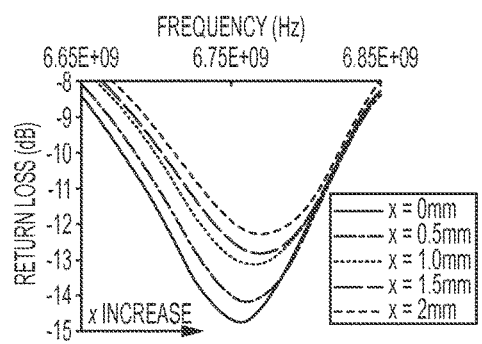
FIG. 19B illustrates graphically an effect of lateral displacement of the reflector on a second resonant frequency of the antenna sensor of FIG. 18A.
Figure 19C:
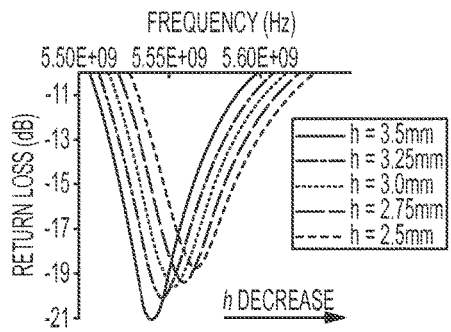
FIG. 19C illustrates graphically an effect of a vertical displacement of the reflector on a first resonant frequency of the antenna sensor of FIG. 18A.
Figure 19D:
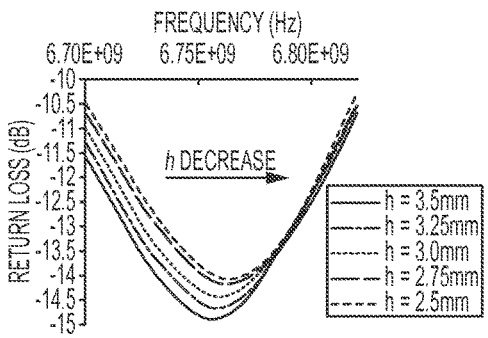
FIG. 19D illustrates graphically an effect of a vertical displacement of the reflector on a second resonant frequency of the antenna sensor of FIG. 18A.

FIGS. 19a, 19b, 19c, 19d illustrate S11 curves of the sensor under pure pressure and pure shear deformation. Referring to FIG. 19a, at h=3.5 mm, the TM10 resonant frequency decreases with increase in shear displacement while, referring to FIG. 19b, the TM01 resonant frequency increases with increase in shear displacement. Referring to FIGS. 19c and 19d, for zero shear displacement (i.e. δx=0), the resonant frequencies of both TM10 and TM01 modes increased when the distance h was reduced (i.e., normal pressure is applied).

Figure 20A:
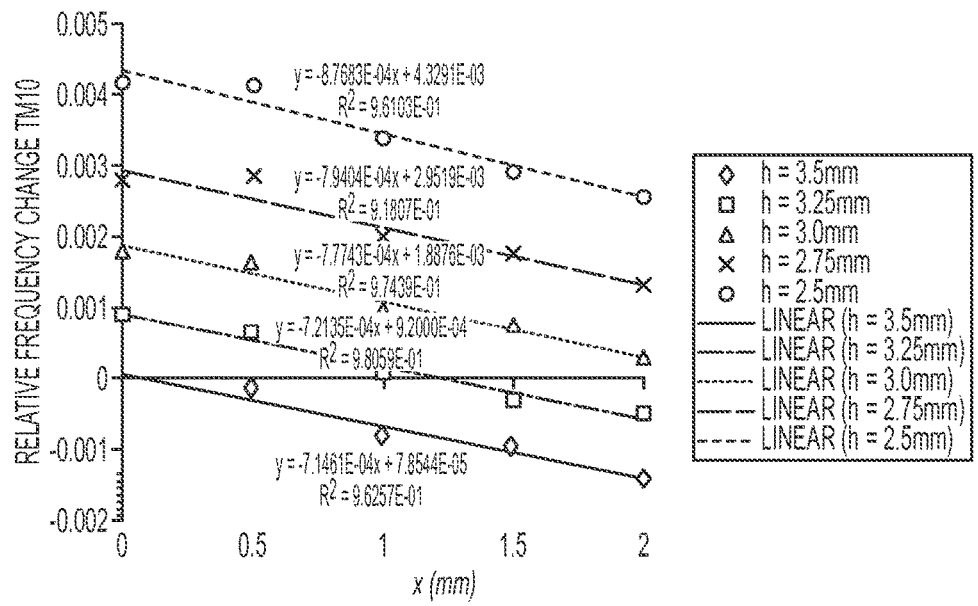
FIG. 20A illustrates graphically an effect of lateral displacement and vertical displacement of the reflector on a first resonant frequency of the antenna sensor of FIG. 18A.
Figure 20B:
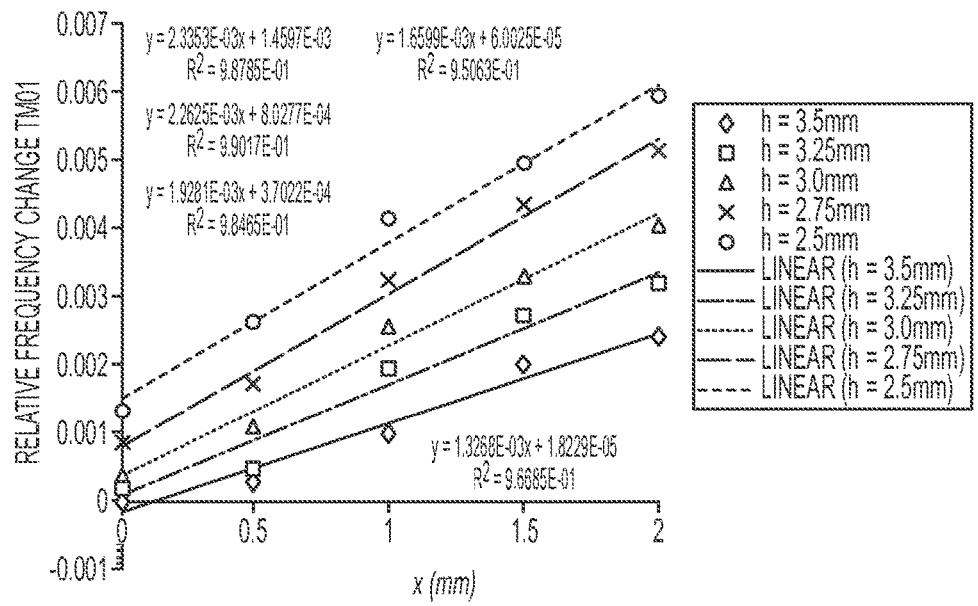
FIG. 20B illustrates graphically an effect of a lateral displacement and a vertical displacement on a second resonant frequency of the antenna sensor of FIG. 18A.

Referring to FIGS. 20a and 20b, the linear relationship between the relative resonant frequency shift and the shear displacement at different normal pressures are shown. Here, the shear sensitivity of the relative TM10 frequency varied from around 0.071% to 0.088% per one millimeter of shear displacement while the shear sensitivity of the relative TM01 frequency varied from around 0.13% to 0.23% per millimeter of shear displacement. The differences in the shear sensitivities of the two resonant frequencies of the antenna 210 indicate the shear and pressure effects from these two resonant frequencies of the antenna 210 can be decoupled.

Alternative Reflectors FIG. 21

Referring to FIGS. 21a, 21b, 21c, the reflector 212 can have a shape other than an L-shape. Referring to FIG. 21a, a reflector 212 has an I-shape and is located along one edge of the radiation patch 214. Referring to FIGS. 21b and 21c, the reflectors 212 are U-shaped reflector and cover three edges of the radiation patch 214. The three edges covered by the reflector 212 of FIG. 21b are different than the three edges covered by the reflector 212 of FIG. 21c. Referring to FIG. 21d, a reflector 212 includes a cross-shaped slot 224.

The shape of the reflector 212 can be used to tune the shear and pressure sensitivities of the antenna sensor. The reflector in designed so that the lateral shift of the reflector primarily affects the radiation pattern of one mode but has small influence on the radiation pattern of the other mode. In general, each reflector defines a reflector area around or adjacent a slot or cutout portion of the reflector.

Figure 22:
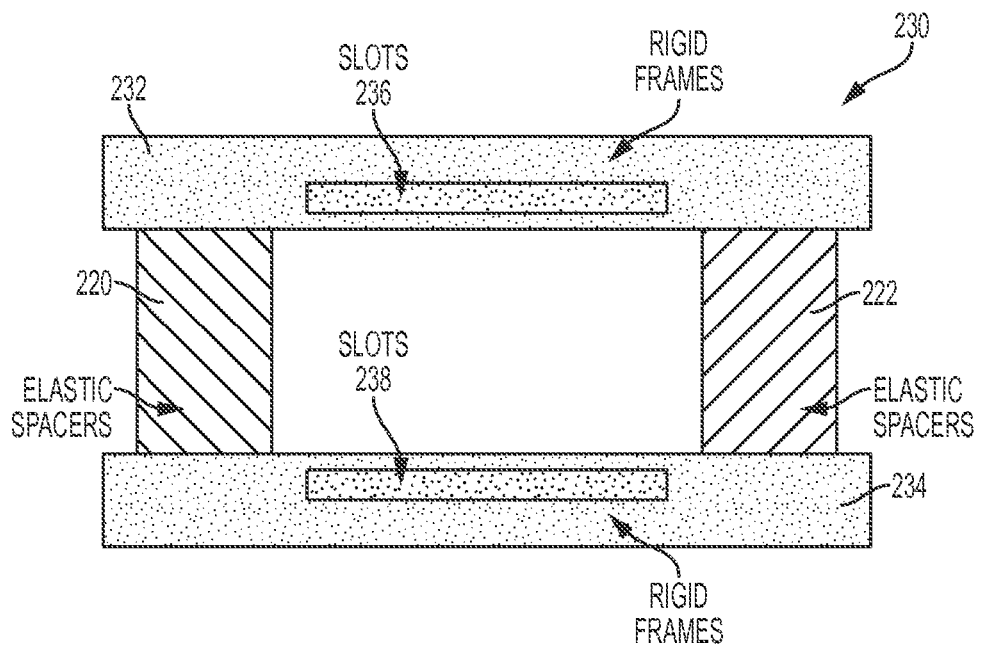
FIG. 22 illustrates an end view of a schematic of a sensor structure associated with the antenna sensor of FIG. 18A.

Sensor Structure and Assembly FIG. 22

Referring to FIG. 22, the patch antenna 210 and the reflector 212 can be fabricated using an etching method. Three dimensional printing can be used to fabricate a sensor structure 230 including the spacer structures 220, 222. Rather than substrates, the sensor structure 230 includes rigid frames 232, 234. An upper rigid frame 232 includes an upper slot 236 and a lower rigid frame 234 includes a lower slot 238. In this embodiment, the sensor 200 is assembled by inserting the patch antenna 210 into the lower slot 238 and the reflector 212 into the upper slot 236. Because three dimensional printers can use different plastics as ink, the modulus of elasticity of the elastic spacers 220, 222 can be selected to control the shear and pressure sensitivity of the sensor 200.

Figure 23:
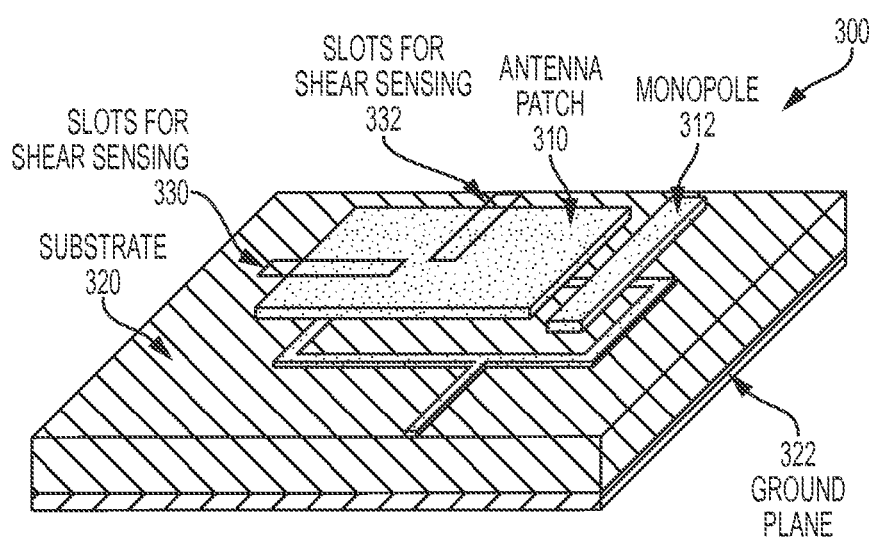
FIG. 23 illustrates a perspective view of an antenna sensor according to an illustrative embodiment.

Sensor with Monopole Antenna and Patch Antenna FIG. 23

As described above, thin microstrip antenna sensors are used to measure shear and pressure wireless interrogation and sensor multiplexing techniques have been developed for distributed antenna sensor arrays. A monopole patch sensor 300 is now described.

Referring to FIG. 23, the monopole patch sensor 300 includes an antenna array. The antenna array includes an antenna patch 310 and an antenna monopole 312. The monopole patch sensor 300 includes a substrate 320 and a ground plane 322. The antenna array is on one side of the substrate 320 and the ground plane 322 is on the opposite side of the substrate 320.

The antenna array is configured for sensing tri-axial stress. Each antenna 310, 312 is an electro-magnetic (EM) resonator that radiates at specific resonant frequencies. The resonant frequencies of the antennas 310, 312 are determined by parameters including the dimensions of the radiation element (e.g. antenna patch or monopole), the dielectric constant of the substrate 320, a thickness of the substrate 320, and conditions of the ground plane 322. A change in one or more of these parameters results in a shift in resonant frequency of the antenna 310, 312.

The monopole patch sensor 300 can be designed to be only sensitive to a single parameter. Additionally, the data from multiple antenna sensors can be fused together to extract multiple modalities.

For bi-directional shear sensing, two slots 330, 332 are cut in the ground plane 322 underneath the antenna patch 310. Each slot 330, 332 increases the equivalent dimensions (e.g., effective electrical length) of the antenna patch 310 along its perpendicular direction. A shear force will shift the antenna patch 310 laterally with respect to the slot 330, 332 and thus changes the overlapping length between the slot 330, 332 and the antenna patch 310, which in turn alters the equivalent dimension (e.g., effective electrical length) of the antenna patch 310. The magnitude and direction of the shear stresses can then be detected from the two frequencies, corresponding to each slot 330, 332, of the antenna patch 310.

In alternative embodiments, the ground plane 322 is replaced by the reflector 212 of FIG. 21d and the cross-shaped cutout 224 is positioned under the patch antenna 310.

In addition, the frequencies of both antennas 310, 312 are sensitive to the height of the substrate 320, which is proportional to the normal pressure applied to the sensor 300. Because the monopole antenna 312 is sensitive to pressure but not shear stress (e.g., the monopole antenna 312 does not overlap the slots 330, 332), pressure is measured from the frequency shift monopole antenna 312. Once the pressure is known, shear information is extracted from the measurements of the patch antenna 310.

Stress Measurement

According to an exemplary embodiment, the monopole patch sensor 300 is embedded in liner materials to monitor stump-socket interface stresses. For stress measurement applications, tissue is isolated from the radiation elements of the antennas 310, 312 by placing the antenna ground plane 322 between the tissues and the antenna radiation elements 310, 312.

Figure 24:
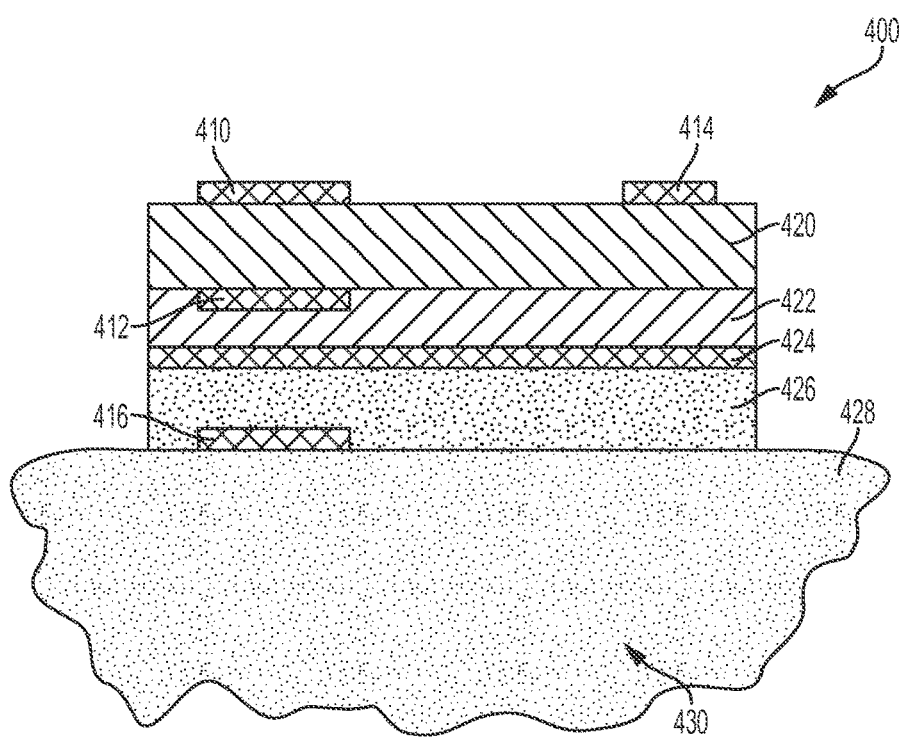
FIG. 24 illustrates a schematic elevational view of an antenna sensor according to illustrative embodiments.

Sensor with Bio-Impedance Antenna FIG. 24

Referring to FIG. 24, according to another exemplary embodiment, a monopole patch antenna sensor 400 is implemented for use in bio-impedance measurements. The monopole patch antenna sensor 400 includes a reflector 410 that is aligned with a patch antenna 412, a dipole antenna 414, and a bio-impedance antenna 416. A superstrate 420 is layered on a first substrate 422, which is layered on a ground plane 424, which is layered on a second substrate 426, which is layered on tissues 428 of a residual limb. For example, the reflector 410 is the reflector 212 of FIG. 21D with the cross-shaped slot 224.

The reflector 410 is aligned with the patch antenna 412 such that lateral deformation of the superstrate 420 in response to a shear stress on the sensor 400 shifts a resonant frequency of the patch antenna 412. Because the dipole antenna 414 is sensitive to pressure but not shear stress (e.g., the dipole antenna 414 does not align with a slotted reflector or overlap the slots in the ground plane 424), pressure is measured from the frequency shift of the dipole antenna 414. Once the pressure is known, shear information can be determined from the frequency shift of the patch antenna 412.

The bio-impedance antenna 416 is sensitive to bio-impedance but not shear because the ground plane 424 does not include a slot. Tor bio-impedance sensing, conductive material (e.g., the ground plane 322) is not placed between the radiation element of the bio-impedance antenna 416 and tissues 428 of a residual limb. Rather, the second substrate 426 and the bio-impedance antenna 416 are positioned in between the tissues 428 and the ground plane 424.

Here, the tissues 424 are essentially a part of the bio-impedance antenna 416 in that a change in a fluid volume 430 in the tissue 424 alters the equivalent dielectric constant of the antenna 416. As described above, pressure is measured from the frequency shift of the dipole antenna 414. Once the pressure is known, bio-impedance can be determined from the frequency shift of the patch antenna 412.

Generally, using measurements from each of the antenna patch 410, the dipole antenna 312, and the bio-impedance antenna 412, each of the bio-impedance, the shear, and the pressure can be determined. For example, independent measurements allow frequency-shifting effects due to bio-impedance, shear, and pressure to be decoupled from one another.

Figure 25:
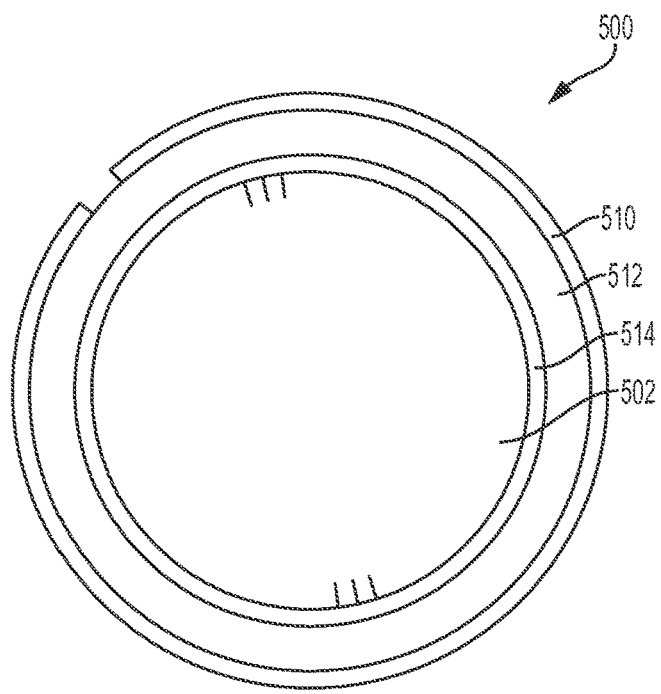
FIG. 25 illustrates a schematic cross-sectional view of an antenna sensor according to illustrative embodiments.

Limb Circumference FIG. 25

According to another exemplary embodiment, a monopole patch antenna sensor 500 is implemented for use in determining circumference of a limb 502. The antenna sensor 500 includes a long dipole antenna 510, a substrate 512, and a reflector 514 (e.g., a ground plane). The sensor 500 is wrapped around the residual limb.

The reflector 514, such as a copper film, is inserted between the antenna 510 and the residual limb 502 to isolate the dipole antenna 510 from the tissues of the residual limb 502. The antenna 510 is fabricated on the substrate 512 (a flexible liner material) that tightly fits the residual limb 502. The substrate material affects the resonant performance of the antenna 510, and also determines the linearity, hysteresis, and sensitivity of the shear/pressure antenna 510. In addition, the substrate material may affect the users' perception of the socket interface. The substrate material can be a commonly used liner materials with acceptable mechanical and electric properties.

As the length of the dipole antenna 510 changes with the volume of residual limb 502, the resonant frequency of the antenna 510 shifts. The antenna 510 can be operated at 8-10 GHz to achieve a trade-off between sensor size (~10 mm in length), sensitivity, and the costs of the interrogation devices. Due to the small sizes of the antenna 510, the curvature of a residual limb 502 is not expected to have any effect on their radiation characteristics. The circumference sensor 500 can have an operating frequency that is lower due to the size of the residual limb 502.

Sensor Insert Fabrication

A vacuum-assisted lamination technique can be used to fabricate the sensor 500, layer-by-layer, using four layers of flexible film materials. First, a positive plaster mold is made to replicate a residual limb 502. A common liner material, to provide the same coefficient of friction and feel for the user, is pulled on the mold and the outer surface is sprayed with heat activated glue. The ground plane 514 for the shear/pressure and circumference sensor 500 as well as the radiation elements 510 and transmission lines of the bio-impedance sensors are patterned on a thin copper film using laser machining, taped on the liner 512, and sprayed with the glue. Subsequently, the middle liner that serves as the substrate 512 for the antenna sensors is pulled over the mold.

After applying the glue, the radiation elements 510 and transmission lines of the stress and circumference sensors, as well as the ground plane 514 of the bio-impedance sensors, again laser machined on a copper film, are taped on the middle liner to complete the lay-up process. Following the lay-up, the entire assembly is vacuum bagged so that controlled pressure can be applied to ensure uniform bonding. Finally, the heat activated glue is cured by placing the vacuum bag in an oven at a prescribed temperature and curing time. For example, the finished sensor insert is around 5-6 mm thick.

Simultaneous Interrogation of Multiple Antenna Sensors

The law does not require and it is economically prohibitive to illustrate and teach every possible embodiment of the present claims. Hence, the above-described embodiments are merely illustrations of implementations set forth for a clear understanding of the principles of the invention. Variations, modifications, and combinations may be made to the above-described embodiments without departing from the scope of the claims. All such variations, modifications, and combinations are included herein by the scope of this disclosure and the following claims.

What is claimed is:

1. An antenna sensor assembly, comprising:
   a first structure and a second structure, wherein the first structure is connected to and spaced apart from the second structure by an intermediate structure;
   wherein the intermediate structure is configured to allow the first structure to displace laterally relative to the second structure in a first direction in response to a shear force;
   the first structure comprising a reflector, wherein the reflector comprises a conductive material and a reflector area; and
   the second structure comprising a patch antenna, wherein the patch antenna comprises:
      a radiation patch that radiates an electromagnetic wave, the radiation patch comprising an antenna area;
      a dielectric substrate; and
      a ground plane;
   wherein an overlapping area is a portion of the antenna area that is overlapped by the reflector area; and
   wherein the patch antenna and the reflector are configured such that resonant frequencies of the antenna sensor assembly are based on a position of the reflector with respect to the patch antenna; and
   wherein lateral displacement of the first structure relative to the second structure in response to a shear force shifts a lateral position of the reflector relative to the patch antenna and thereby changes a size of the overlapping area.

2. The antenna sensor assembly of claim 1, wherein the resonant frequencies of the antenna sensor assembly are based on the overlapping area.

3. The antenna sensor assembly of claim 1, wherein the intermediate structure is configured to allow the first structure to displace vertically relative to the second structure; wherein vertical displacement of the second structure relative to the first structure shifts a vertical position of the reflector relative to radiation patch; and
   wherein the patch antenna and the reflector are configured such that resonant frequencies of the antenna sensor assembly are further based on a vertical position of the reflector with respect to the patch antenna.

4. The antenna sensor assembly of claim 1, wherein the reflector is a metallic reflector.

5. The antenna sensor assembly of claim 4, wherein the metallic reflector is shaped and positioned such that when the first structure is not displaced:
   the reflector area overlaps a first edge of the antenna area; and
   at least a second edge of the antenna area is at least in part not overlapped by the reflector area.

6. The antenna sensor assembly of claim 5, wherein the reflector area overlaps a third edge of the patch antenna.

7. The antenna sensor assembly of claim 6, wherein the reflector area overlaps a fourth edge of the antenna area.

8. The antenna sensor assembly of claim 6, wherein a fourth edge of the antenna area is at least in part not overlapped by the reflector area.

9. The antenna sensor assembly of claim 1, wherein the reflector area includes a first strip that extends longitudinally in a second direction, wherein the second direction is perpendicular to the first direction.

10. The antenna sensor assembly of claim 9, wherein the reflector area includes a second strip that extends longitudinally in the first direction.

11. The antenna sensor assembly of claim 1, wherein the reflector area has a shape that is one of a strip, an L-shape, an I-shape, a U-shape, and a cross-shape.

12. The antenna sensor assembly of claim 1, wherein a shape of the reflector area at least partially defines a shape of a non-reflector area of the first structure.

13. The antenna sensor assembly of claim 12, wherein a non-overlapping area is a portion of the antenna area that is overlapped by the non-reflector area.

14. The antenna sensor assembly of claim 13, wherein the shape of the non-reflector area has a shape that is one of a slot, a strip, and a cross-shape.

15. The antenna sensor assembly of claim 1, wherein the intermediate structure is a spacer that is configured to prevent the first structure from displacing laterally relative to the second structure in a second direction in response to a shear force, wherein the first direction is perpendicular to the second direction.

16. The antenna sensor assembly of claim 15, wherein the first structure includes a first rigid frame and the second structure includes a second rigid frame; and
   wherein the first rigid frame includes a first slot that is configured to receive the reflector and the second rigid frame includes a second slot that is configured to receive the patch antenna.

17. The antenna sensor assembly of claim 1, wherein the intermediate structure is a dielectric substrate.

* * * * *